US005834425A

United States Patent [19]

Tedder et al.

[11] Patent Number: 5,834,425
[45] Date of Patent: Nov. 10, 1998

[54] USE OF CHIMERIC SELECTINS AS SIMULTANEOUS BLOCKING AGENTS FOR COMPONENT SELECTIN FUNCTION

[75] Inventors: Thomas F. Tedder, S. Natick; Geoffrey S. Kansas, Watertown, both of Mass.

[73] Assignee: Dana-Farber Cancer Institute, Inc., Boston, Mass.

[21] Appl. No.: 461,592

[22] Filed: Jun. 5, 1995

Related U.S. Application Data

[62] Division of Ser. No. 340,539, Nov. 16, 1994, which is a continuation of Ser. No. 8,459, Jan. 25, 1993, abandoned, which is a continuation-in-part of Ser. No. 983,606, Nov. 30, 1992, which is a continuation of Ser. No. 730,503, Jul. 8, 1991, abandoned, and Ser. No. 313,109, Feb. 21, 1989, abandoned, and a continuation-in-part of Ser. No. 700,773, May 15, 1991, abandoned, Ser. No. 737,092, Jul. 29, 1991, abandoned, Ser. No. 770,608, Oct. 3, 1991, abandoned, and Ser. No. 862,483, Apr. 2, 1992, Pat. No. 5,389,520.

[51] Int. Cl.⁶ .................................................. A61K 38/16
[52] U.S. Cl. .............................. 514/12; 424/134.1; 514/2
[58] Field of Search ........................ 514/2, 12; 424/134.1

[56] References Cited

U.S. PATENT DOCUMENTS

| | | | |
|---|---|---|---|
| 4,783,330 | 11/1988 | Furie et al. | 424/1.1 |
| 5,026,537 | 6/1991 | Daddona et al. | 424/1.1 |
| 5,081,034 | 1/1992 | Bevilacque et al. | 435/252.33 |
| 5,098,833 | 3/1992 | Lasky et al. | 435/69.1 |
| 5,116,964 | 5/1992 | Capon et al. | 536/723.5 |
| 5,216,131 | 6/1993 | Lasky et al. | |

FOREIGN PATENT DOCUMENTS

| | | |
|---|---|---|
| WO 91/07993 | 6/1991 | WIPO . |
| WO 92/12994 | 8/1992 | WIPO . |
| WO 92/20712 | 11/1992 | WIPO . |

OTHER PUBLICATIONS

Springer Nature 346, 425–435, 1990.
Kansas et al. J. Cell Biol. 114,351–358, 1991.
Aizawa et al., "Molecular basis of the recognition of intraveneously transplanted hemopoietic cells by bone marrow," Proc. Natl. Acad. Sci. USA 85:3180–3183 (1988).
Bargatze et al., "High Endothelial Venule Binding as a Predictor of the Dissemination of Passaged Murine Lymphomas," J. Exp. Med. 166:1125–1131 (1987).
Berg et al., "Homing Receptors and Vascular Addressins: Cell Adhesion Molecules that Direct Lymphocyte Traffic," Immunol. Rev. 108:421–427 (1989).
Bevilacqua et al., "Endothelial Leukocyte Adhesion Molecule 1: An Inducible Receptor for Neutrophils Related to Complement Regulatory Proteins and Lectins," Science 243:1160–1165 (1989).
Bevilacqua et al., "Identification of an inducible endothelial–leukocyte adhesion molecule," Proc. Natl. Acad. Sci. USA 84:9238–9242 (1987).
Bowen et al., "Characterization of a Human Homologue of the Murine Peripheral Lymph Node Homing Receptor," J. Cell Biol. 109:421–427 (1989).
Butcher et al., "Lymphocyte Adherence to High Endothelial Venules: Characterization of a Modified In Vitro Assay, and Examination of the Binding of Syngenic and Allogenic Lymphocyte Populations," J. Immunol. 123:1996–2003 (1979).
Camerini et al., "Leu–8/TQ–1 is the human equivalent of the Mel–14 lymph node homing receptor," Nature 342:78–82 (1989).
Carbone et al., "Expression of Leu–8 Surface Antigen in B–Cell Lymphomas. Correlation with Other B–Cell Markers," J. Pathol. 154:133–140 (1988).
Chin et al., "Lymphocyte Recognition of Lymph Node High Endothelium. I. Inhibition of In Vitro Binding by a Component of Thoracic duct Lymph," J. Immunol. 125:1764–1769 (1980).
Chin et al., "Lymphocyte Recognition of Lymph Node High Endothelium. II. Characterization of an In Vitro Inhibitory Factor Isolated by Antibody Affinity Chromatography," J. Immunol. 125:1770–1774 (1980).
Chin et al., "Lymphocyte Recognition of Lymph Node High Endothelium. V. Isolation of Adhesion Molecules from Lysates of Rat Lymphocytes," J. Immunol. 131:1368–1374 (1983).
Collins et al., "Structure and Chromosomal Location of the Gene for Endothelial–Leukocyte Adhesion Molecule 1," J. biol. chem. 266:2466–2473 (1991).
Dana et al., "Two Functional Domains in the Phagocyte Membrane Glycoprotein Mo 1 identified with Monoclonal Antibodies," J. Immunol. 137:3259–3263 (1986).
DiStefano et al., "Identification of a truncated form of the nerve growth factor receptor," Proc. Natl. Acad. Sci. USA 85:270–274 (1988).
Dowbenko et al., "Characterization of the Murine Homing Receptor Gene Reveals Correspondence between Protein Domains and coding Exons," Genomics 9:270–277 (1991).
Downing et al., "Ligand and Protein Kinase C Downmodulate the Colony Stimulating Factor 1 Receptor by Independent Mechanisms," Mol. cell. Biol. 9:2890–2896 (1989).

(List continued on next page.)

Primary Examiner—David L. Fitzgerald
Assistant Examiner—Karen E. Brown
Attorney, Agent, or Firm—Fish & Neave; James F. Haley, Jr.; Jane T. Gunnison

[57] ABSTRACT

Chimeric peptides or polypeptides that combine ligand binding portions from within the lectin and EGF domains of two different selectins are disclosed. The peptides or polypeptides can be constructed solely of the indicated portions of lectin or EGF domains or they can include portions of any of the remaining domains (SCR, transmembrane or cytoplasmic), or the entire extracellular portion, of a generic selectin molecule. The peptides or polypeptides also can be joined to a carrier protein (e.g., a soluble portion of an immunoglobulin molecule) to increase the serum half-life of the therapeutic agent. The chimeric polypeptides can be used as therapeutic agents to antagonize selectin function. They are also useful for screening for agents that are simultaneously antagonists of the function of lectin and EGF domains of different selectins.

8 Claims, 14 Drawing Sheets

OTHER PUBLICATIONS

Drickamer et al., "Complete amino acid sequence of a membrane receptor for glycoproteins," J. Biol. Chem. 256:5827–5839 (1981).

Drickamer et al., "Two Distinct Classes of Carbohydrate–recognition Domains in Animal Lectins," J. Biol. Chem. 263:9557–9560 (1988).

Duijvestijn et al., "Mechanisms and regulation of lymphocyte migration," Immunol. today 10:23–28 (1989).

Ezekowitz et al., "A human mannose–binding protein is an acute–phase rectant that shares sequence homology with other vertebrate lectins," J. Exp. Med. 167:1034–1046 (1988).

Gallatin et al., "Lymphocyte Homing Receptors," Cell 44:673–680 (1986).

Gallatin et al., "A cell–surface molecule involved in organ–specific homing of lymphocytes," Nature 304:30–34 (1983).

Gatenby et al., "Dissection of Immunoregulatory Subpopulations of T Lymphocytes within the Helper and Suppressor Sublineages in Man," J. Immunol. 129:1997–2000 (1982).

Geng et al., "Rapid neutrophil adhesion to activated endothelium mediated by GMP–140," Nature 323:757–760 (1990).

Goldstein et al., "A Human Lymphocyte Homing Receptor, the Hermes Antigen, is Related to Catilage Proteoglycan Core and Link Proteins," Cell 56:1063–1072 (1989).

Gregory, "Isolation and structure of urogastrone and its relationship to epidermal growth factor," Nature 257:325–327 (1975).

Griffin et al., "Granulocyte–Macrophage Colony–Stimulating Factor and Other Cytokines Regulate Surface Expression of the Leukocyte Adhesion Molecule–1 on Human Neutrophils, Monocytes, and their Precursors," J. Immunol. 145:576–584 (1990).

Hallmann et al., "The peripheral lymph node homing receptor, LECAM–1, is involved in CD18–independent adhesion of human neutrophils to endothelium," Biochem. Biophys. Res. Comm. 174:236–243 (1991).

Harlow et al., "Antibodies: A Laboratory Manual," Cold Spring Harbor (1988).

Harris et al., "Therapeutic Antibodies—the Coming of Age," Tibtech 11:42–44 (1993).

Hidaka et al., "Isoquinolinessulfonamides, Novel and Potent Inhibitors of Cyclic Nucleotide Dependent Protein Kinase and Protein Kinace C," Biochemistry 23:5036–5041 (1984).

Hildreth et al., "The Human Lymphocyte Function–Associated (HFLA) Antigen and a Related Macrophage Differentiation Antigen HMac–1): Functional Effects of Sub-unit–Specific Monoclonal Antibodies," J. Immunol. 134:3272–3280 (1985).

Ichinose et al., "Amino–Acid Sequence of the b Subunit of Human Factor XIII, a Protein Composed of Ten Repetitive Segments," Biochemistry 25:4633–4638 (1986).

Imai et al., "Identification of a carbohydrate–based endothelial ligand for a lymphocyte homing receptor," J. Cell Biol. 113:1213–1221 (1991).

Jalkanen et al., "Lymphocyte Recognition of High Endothelium: Antibodies to Distinct Epitopes of an 85–95–kD Glycoprotein Antigen Differentially Inhibit Lymphocyte Binding to Lymph Node, Mucosal, or Synovial Endothelial Cells," J. Cell Biol. 105:983–990 (1987).

Johnson, G.J., et al., "Thromboxane unresponsive dog platelets have an abnormal thromboxane $A_2$/prostaglandin $H_2$ receptor–linked G protein," Blood Suppl. 72:327A (1988).

Johnston, G.I., et al., "Cloning of GMP–140, a Granule Membrane Protein of Platelets and Endothelium: Sequence Similarity to Proteins Involved in Cell Adhesion and Inflammation," Cell 56:1033–1044 (1989).

Johnston, G.I., et al "Structure of the Human Gene Encoding Granule Membrane Protein–140, a Member of the Selectin Family of Adhesion Receptors for Leukocytes," J. Biol. Chem. 265:21381–21385 (1990).

Jung et al., "Rapid Modulation of Homing Receptors ($gp90^{MEL-14}$) induced by Activators of Protein Kinase C," J. Immunol. 144:130–136 (1990).

Jutila et al., "Characterization of a Functionally Important and Evolutionarily Well–Conserved Epitope Mapped to the Short Consensus Repeats of E–Selectin and L–Selectin," J. Exp. Med. 175:1565–1573 (1992).

Jutila et al., "Function and Regulation of the Neutrophil MEL–14 Antigen In Vivo: Comparison with LFA–1 and MAC–1," J. Immunol. 143:3318–3324 (1989).

Kanof et al., "Leu–8 Antigen Expression is Diminished During Cell Activation But Does Not Correlate With Effector Function of Activated T Lymphocytes," J. Immumol. 140:3701–3706 (1988).

Kansas et al., "Molecular Mapping of Functional Domains of the Leukocyte Receptor for Endothelium, LAM–1," J. Cell Biol. 114:351–358 (1991).

Kansas et al., "Expression of Adhesion Structures During B Cell Development in Man," J. Immunol. 142:3058–3062 (1989).

Kansas et al., "A Family of Cell–Surface Glycoproteins Defined by a Putative Anti–Endothelial Cell Receptor Antibody in Man," J. Immunol. 142:3050–3057 (1989).

Kansas et al., "Maturational and Functional Diversity of Human B Lymphocytes Delineated with Anti–Leu–8," J. Immunol. 134:3003–3006 (1985).

Kikutani et al., "Molecular Structure of Human Lymphocyte Receptor for Immunoglobulin E," Cell 47:657–665 (1986).

Kishimoto et al., "Antibodies Against Human Neutrophil LECAM–1 (LAM–1/Leu–8/DREG–56 Antigen) and Endothelial Cell ELAM–1 Inhibit a Common CD 18–Independent Adhesion Pathway In Vitro," Blood 78:805–811 (1991).

Kishimoto et al., "Identification of a Human Peripheral Lymph Node Homing Receptor: A Rapidly Down–Regulated Adhesion Molecule," Proc. Natl. Acad. Sci. USA 87:2244–2248 (1990).

Kishimoto et al., "Neutrophil Mac–1 and MEL–14 Adhesion Proteins Inversely Regulated by Chmotactic Factors," Science 245:1238–1241 (1989).

Klickstein et al., "Human C3b/C4b Receptor (CR1): Demonstration of Long Homologous Repeating Domains That Are Composed of the Short Consensus Repeats Characteristic of C3/C4 Binding Proteins," J. Exp. Med. 165:1095–1112 (1987).

Kozak et al., "Point Mutations Define a Sequence Flanking the AUG Initiator Codon That Modulates Translation by Eukaryotic Ribosome," Cell 44:283–292 (1986).

Krusius et al., "A Fibroblast Chondroitin Sulfate Proteoglycan Core Protein Contains Lectin–like and Growth Factor–like Sequences," J. Biol. Chem. 262:13120–13125 (1987).

Kurk et al., "Characterization of an Endothelial Cell Antigen Recognized by an Anti–Leukocyte Homing Receptor (L–Selectin) Monoclonal Antibody," FASEB J. 6:A1142 (1992).

Larsen et al., "PADGEM–Dependent adhesion of platelets to monocytes and neutrophils sis mediated by a lineage–specific carbohydrate, LNF III (CD 15)," Cell 63:467–474 (1990).

Larsen et al., "PADGEM Protein: A receptor that mediates the Interaction of activated platelets with neutrophils and monocytes," Cell 59:305–312 (1989).

Lasky et al., "Cloning of a Lymphocyte Homing Receptor Reveals a Lectin Domain," Cell 56:1045–1055 (1989).

Lasky, "Selectins: Interpreters of Cell–Specific Carbohydrate Information During Inflammation," Science 258:964–969 (1992).

Leonard et al., "Molecular cloning and expression of cDNAs for the human interleukin–2 receptor," Nature 311:626–631 (1984).

Lewinsohn et al., "Leukocyte–endothelial cell recognition: Evidence of a common molecular mechanism shared by neutrophils, lymphocytes, and other leukocytes," J. Immunol. 138:4313–4321 (1987).

Ley et al., "Lectin–Like Cell Adhesion Molecule 1 Mediates Leukocyte Rolling in Mesenteric Venules In Vivo," Blood 77:2553–2555 (1991).

Luscinskas et al., "Cytokine–activated human endothelial monolayers support enhanced neutrophil transmigration via a mechanism involving both endothelial–leukocyte adhgesion molecule–1 and intercellular adhesion molecule–1," J. Immunol. 146:1617–1625 (1989).

Luscinskas et al., "Endothelial–leukocyte adhesion molecule–1–dependent and leukocyte (CD11/CD18)–dependent mechanisms contribute to polymorphonuclear leukocyte adhesion to cytokine–activated human vascular endothelium," J. Immunol. 142:2257–2263 (1989).

Marx, "New Family of Adhesion Proteins Discovered," Science 243:1144 (1989).

Michie et al., "Expression of the Leu–8 Antigen by B–Cell Lymphomas," Am. J. Clin. Pathol. 88:486–490 (1987).

Miyake et al., "Hyaluronate Can Function as a Cell Adhesion Molecule and CD44 Participates in Hyaluronate Recognition," J. Exp. Med. 172:69–75 (1990).

Morley et al., "Internal homologies of the Ba fragment from human complement component Factor B, a class III MHC ANTIGEN," EMBO J. 3:153–157 (1984).

Nojima et al., "VLA–4 Mediates CD3–dependent CD4$^+$T Cell Activation Via the CS1 Alternatively Spliced Domain of Fibronectin," J. Exp. Med. 172:1185–1192 (1990).

Ord et al., "Structure of the Gene Encoding the Human Leukocyte Adhesion Molecule–1 (TQ1, Leu–8) of Lymphocytes and Neutrophils," J. Biol. Chem. 265:7760–7767 (1990).

Osborn, "Leukocyte Adhesion to Endothelium in Inflammation," Cell 62:3–6 (1990).

Pals et al., "Expression of Lymphocyte Homing Receptor as a Mechanism of Dissemination in Non–Hodgkin's Lymphoma," Blood 73:885–888 (1989).

Picker et al., "The Neutrophil Selectin LECAM–1 Presents Carbohydrate Ligands to the Vascular Selectins ELAM –1 and GMP–140," Cell 66:921–933 (1991).

Polte et al., "Full length vascular cell adhesion molecule 1 (VCAM–1)," Nuc. Acids Res. 18:5901 (1990).

Porteau et al., "Shedding of Tumor Necrosis Factor Receptors by Activated Human Neutrophils," J. Exp. Med. 172:599–607 (1990).

Reinherz et al., "Heterogeneity of Human T4 Inducer T cells Defined by a Monoclonal Antibody that Delineates Two Functional Subpopulations," J. Immunol. 128:463–468 (1982).

Rice et al., "Vascular and Nonvascular Expression of INCAM–110," Amer. J. Pathol. 138:385–393 (1991).

Rice et al., "An Inducible Endothelial Cell Surface Glycoprotein Mediates Melanoma Adhesion," Science 246:1303–1306 (1989).

Rosen et al., "Involvement of Sialic Acid on Endothelial Cells in Organ–Specific Lymphocyte Recirculation," Science 228:1005–1007 (1985).

Rothlein et al., "A Human Intercellular Adhesion Molecular (ICAM–1) Distinct From LFA–1," J. Immunol. 137:1270–1274 (1986).

Rothlein et al., "A Form of Circulating ICAM–1 in Human Serum," J. Immunol. 147:3788–3793 (1991).

Sanchez–Madrid et al., "Three distinct antigens associated with human T–lymphocyte–mediated cytolysis: LFA–1, LFA–2, and LFA–3," Proc. Natl. Acad. Sci. USA 79:7489–7493 (1982).

Sher et al., "Homing Receptors and Metastasis," Adv. Can. Res. 51:361–389 (1988).

Siegelman et al., "The mouse lymph node homing receptor is identical with the lymphocyte cell surface marker Ly–22: Role of the EGF domain in endothelial binding," Cell 61:611–622 (1990).

Siegelman et al., Human homologue of mouse lymph node homing receptor: Evolutionary conservation at tandem cell interaction domains, Proc. Natl. Acad. Sci. USA 86:5562–5566 (1989).

Siegelman et al., "Mouse Lymph Node Homing Receptor cDNA Clone Encodes a Glycoprotein Revealing Tandem Interactions Domains," Science 243:1165–1172 (1989).

Smith et al., "Chemotactic factors regulate lectin adhesion molecule 1 (LECAM–1)–dependent neutrophil adhesion to cytokine–stimulated endothelial cells In Vitro," J. Clin. Invest. 87:609–618 (1991).

Spertini et al., "Function and Evolutionary Conservation of Distinct Epitopes on the Leukocyte Adhesion Molecule–1 (TQ–1, Leu–8) that Regulate Leukocyte Migration," J. Immunol. 147:942–949 (1991).

Spertini et al., "Leukocyte Adhesion Molecule (LAM–1, L–Selectin) Interacts with an Inducible Endothelial Cell Ligand to Support Leukocyte Adhesion," J. Immunol. 147:2565–2573 (1991).

Spertini et al., "Regulation of Leukocyte Adhesion Molecule–1 (TQ1, Leu–8) Expression and Shredding by Normal and Malignant Cells," Leukemia 5:300–308 (1991).

Spertini et al., "Regulation of leukocyte migration by activation of the leukocyte adhesion molecule–1 (LAM–1) selectin," Nature 349:691–694 (1991).

Spiess et al., "Sequence of a Second Human Asialoglycoprotein Receptor: conservation of Two Receptor Genes During Evolution," Proc. Natl. Acad. Sci. USA 82:6465–6469 (1985).

Springer, "Adhesion receptors of the immune system," Nature 346:425–434 (1990).

Stamekovic et al., "A Lymphocyte Molecule Implicated in Lymph Node Homing is a Member of the Cartilage Link Protein Family," Cell 56:1057–1062 (1989).

Stamper et al., "Lymphocyte Homing into Lymph Nodes: In Vitro Demonstration of the Selective Affinity of Recirculating Lymphocytes for High–Endothelial Venules," J. Exp. Med. 144:828–833 (1976).

Stoolman et al., "Homing Receptors on Human and Rodent Lymphocytes–Evidence for a Conserved Carbohydrate–Binding Specificity," Blood 70:1842–1850 (1987).

Stoolman, "Adhesion Molecules Controlling Lymphocyte Migration," Cell 56:907–910 (1989).

Stoolman et al., "Phosphomannosyl Receptors May Participate in the Adhesive Interaction between Lymphocytes and High Endothelial Venules," J. Cell Biol. 99:1535–1540 (1984).

Stoolman et al., "Adhesion Molecules of Cultured Hematopoietic Malignancies," J. Clin. Invest. 84:1196–1205 (1989).

Strickler et al., "Intermediate Lymphocytic Lymphoma: An Immunophenotypic Study with Comparison to Small Lymphocytic Lymphoma and Diffuse Small Cleaved Cell Lymphoma," Hum. Path. 19:550–554 (1988).

Takahashi et al., "Cloning and Sequencing of cDNA of *Sarcophaga perengrina* Humoral Lectin Induced on Injury of the Body Wall," J. Biol. Chem. 260:12228–12233 (1985).

Tamaoki et al., "Staurosporine, A Potent Inhibitor of Phospholipid/$Ca^{++}$Dependent Protein Kinase," Biochem. Biophys. Res. Comm. 135:397–402 (1986).

Tedder, "Cell–surface Receptor Shedding: A Means of Regulating Function," Am. J. Respir. Cell Mol. Biol. 5:305–307 (1991).

Tedder et al., "Function of the LFA–1 and T4 molecules in the direct activation of resting human B lymphocytes by T lymphocytes," Eur. J. Immunol. 16:1539–1543 (1986).

Tedder et al., "Human antigen–specific memory T cells express the homing receptor (LAM–1) necessary for lymphocyte recirculation," Eur. J. Immunol. 20:1351–1355 (1990).

Tedder et al., "Isolation and Chromosomal Localization of cDNAs Encoding a Novel Human Lymphocyte Cell Surface Molecule, LAM–1," J. Exp. Med. 170:123–133 (1989).

Tedder et al., "Human Lyphocyte Differentiation Antigens HB–10 and HB–11," J. Immunol. 134:2989–2994 (1985).

Tedder et al., "Expression of the Human Leukocyte Adhesion Molecule, LAM–1: Identity with the TQ1 and Leu–8 Differentiation Antigens," J. Immunol. 144:532–540 (1990).

Tedder et al., "Heterogeneity in the B1 (CD20) Cell Surface Molecule Expressed by Human B–Lymphocytes," Molecular Immunol. 25:1321–1330 (1988).

Tedder et al., "Isolation and structure of cDNA encoding the B1 (CD20) cell–surface antigen of human B lymphocytes," Proc. Natl. Acad. Sci. USA 85:208–212 (1988).

True et al., "Requirement for Sialic Acid on the Endothelial Ligand of a Lymphocyte Homing Receptor," J. Cell Biol. 111:2757–2764 (1990).

von Heijne, "A New Method for Predicting Signal Sequence Cleavage Sites," Nucleic Acid Research 14:4683–4690 (1986).

Walcheck et al., "Characterization of the Bovine Peripheral Lymph Node Homing Receptor: A Lectin Cell Adhesion Molecule (LECAM)," Eur. J. Immunol. 22:469–476 (1992).

Watson, M. et al., "Genomic Organization of the Selectin Family of Leukocyte Adhesion Molecules on Human and Mouse Chromosome 1", J. Exp. Med. 172:263–272 (1990).

Watson, S. et al., "A Homing Receptor–IgG Chimera as a Probe for Adhesive Ligands of Lymph Node High Endothelial Venules," J. Cell Biol. 110: 2221–2229 (1990).

Watson, S. et al., "The complement binding–like domains of the murine homing receptor facilitate lectin activity," J. Cell Biol. 115:235–243 (1991).

Watson, S. et al., "Neutrophil influx into an inflammatory site inhibited by a soluble homing receptor–IgG chimera," Nature 349:164–167 (1991).

Weiss et al., "Interactions of cancer cells with the microvasculature during metastasis," FASEB J. 2:12–21 (1988).

Wu et al., "Evolutionarry Conservation of Tissue–specific Lymphocyte–Endothelial Cell Recognition Mechanisms Involved in Lymphocyte Homing," J. Cell Biol. 107:1845–1851 (1988).

Yednock et al., "Phosphomannosyl–derivatized Beads Detect a Receptor Involved in Lymphocyte Homing," J. Cell Biol. 104:713–723 (1987).

Yednock et al., "Receptors Involved in Lymphocyte Homing: Relationship between a Carbohydrate–binding Receptor and the MEL–14 Antigen," J. Cell Biol. 104:725–731 (1987).

Yoshitake et al., "Nucleotide Sequence of the Gene for Human Factor IX (Antihemophilic Factor B)," Biochemistry 25:3736–3750 (1985).

Hsu–Lin et al., "A Platelet Membrane Protein Expressed during Platelet Activation and Secreteion," J. Ciol. Chem. 259:9121–9126 (1984).

Kansas, "Structure and Function of L–Selectin," APMIS 100:287–293 (1991).

Larsen et al., "P–selectin and E–selectin," J. Biol. Chem. 267(16):11104–11110 (1992).

Lax et al., "Functional analysis of the ligand binding site of EGF receptor utilizing chimeric chicken/human receptor molecules." The EMBO Journal pp. 421–427.

Moore et al., "Identification of a Specific Glycoprotein Ligand for P–selectin (CD62) on Myeloid Cells," J. Cell Biology 118(2):445–456 (1992).

Moore et al., "GMP–140 Binds to a Glycoprotein Receptor on Human Neutrophils: Evidence for Lectin–like Interaction," J. Cell Biol. 112(3):491–499 (1991).

Polley et al., "CD62 and endothelial cell–leukocyte adhesion molecule 1 (ELAM–1) recognize the same carbohydrate ligand, sial–Lewis x," Proc. Natl. Sci. USA 88:6224–6228 (1991).

Zhou et al., "The Selectin GMP–140 Binds to Sialylated, Fucosylated Lactosaminoglycans on Both Myeloid and Nonmyeloid Cells," J. Cell Biology 115(2):557–561 (1991).

J.M. Harlan and D.Y. Liu, Eds., "Adhesion: It's Role in Inflammatory Disease," W.H. Freeman (1992).

MONOCLONAL ANTIBODY REACTIVITY

| DESIGNATION | G1 (P LECTIN) | LAM1-3 (L LECTIN) | LAM1-1 (L LECTIN/EGF) | LAM1-14 (L SCR) | S12 (P SCR) |
|---|---|---|---|---|---|
| L-SELECTIN (L) | 0 | 525 | 374 | 576 | 0 |
| P-SELECTIN (P) | 1712 | 0 | 0 | 0 | 1059 |
| P2L | 839 | 0 | 68 | 419 | 0 |
| P3L | 714 | 0 | 0 | 350 | 0 |
| L2P | 19 | 1484 | 0 | 0 | 1093 |
| L3P | 0 | 1779 | 1503 | 0 | 1018 |
| L2P3L | 0 | 363 | 0 | 266 | 0 |

FIG. 1

```
gaattcCCTTT GGGCAAGGAC CTGAGACCCT TGTGCTAAGTCAAGAGGCTCA ATG GGC
                                                         M   G
                                                         1
 C   R   R   T   R   E   G   P   S   K   A   M
TGC AGA AGA ACT AGA GAA GGA CCA AGC AAA GCC ATG              94
                    20
 I   F   P   W   K   C   Q   S   T   Q   R   D   L   W   N   I
ATA TTT CCA TGG AAA TGT CAG AGC ACC CAG AGG GAC TTA TGG AAC ATC
                                    40                        30
 F   K   L   W   G   W   T   M   L   C   C   D
TTC AAG TTG TGG GGG TGG ACA ATG CTC TGT TGT GAT             168
                        50
 F   L   A   H   H   G   T   D   C│W   T   Y   H   Y   S   E
TTC CTG GCA CAT CAT GGA ACC GAC TGC TGG ACT TAC CAT TAT TCT GAA
 K   P   M   N   W   Q   R   A   R   R   F   C
AAA CCC ATG AAC TGG CAA AGG GCT AGA AGA TTC TGC             262
                                        80
 R   D │N   Y   T │D   L   V   A   I   Q   N   K   A   E   I
CGA GAC AAT TAC ACA GAT TTA GTT GCC ATA CAA AAC AAG GCG GAA ATT
            90
 E   Y   L   E   K   T   L   P   F   S   R   S
GAG TAT CTG GAG AAG ACT CTG CCT TTC AGT CGT TCT             346
```

FIG. 4A

```
         100                                         110
  Y   Y   W   I   G   I   R   K   I   G   G   I   W   T   W
 TAC TAC TGG ATA GGA ATC CGG AAG ATA GGA GGA ATA TGG ACG TGG
                                 120
  V   G   T  ┌N   K   S┐  L   T   E   E   A   E   N
 GTG GGA ACC │AAC AAA TCT│CTC ACT GAA GAA GCA GAG AAC  430
             └───────────┘
                 130                                 140
  W   G   D   G   E   P   N   N   K   K   N   K   E   D   C
 TGG GGA GAT GGT GAG CCC AAC AAC AAG AAG AAC AAG GAG GAC TGC
                                     150
  V   E   I   Y   I   K   R   N   K   D   A   G   K
 GTG GAG ATC TAT ATC AAG AGA AAC AAA GAT GCA GGC AAA  514
                         160
  W   N   D   D   A   C   H   K   L   K   A   A   L   C   Y
 TGG AAC GAT GAC GCC TGC CAC AAA CTA AAG GCA GCC CTC TGT TAC
 170                                             180
  T   A   S   C   Q   P   W   S   C   S   G   H   G
 ACA GCT TCT TGC CAG CCC TGG TCA TGC AGT GGC CAT GGA  598
                                 190
  E   C   V   E   I   I   N  ┌N   Y   T┐  C   N   C   D   V
 GAA TGT GTA GAA ATC ATC AAT │AAT TAC ACC│TGC AAC TGT GAT GTG
             200             └───────────┘           210
  G   Y   Y   G   P   Q   C   Q   F   V   I   Q   C
 GGG TAC TAT GGG CCC CAG TGT CAG TTT GTG ATT CAG TGT  682
                                 220
  E   P   L   E   A   P   E   L   G   T   M   D   C   T   H
 GAG CCT TTG GAG GCC CCA GAG CTG GGT ACC ATG GAC TGT ACT CAC
                 230
  P   L   G   N   F   N   F   N   S   Q   C   A   F
 CCT TTG GGA AAC TTC AAC TTC AAC TCA CAG TGT GCC TTC  766
     240                                     250
  S   C   S   E   G   T  ┌N   L   T┐  G   I   E   E   T   T
 AGC TGC TCT GAA GGA ACA │AAC TTA ACT│GGG ATT GAA GAA ACC ACC
                         └───────────┘
                             260
  C   E   P   F   G  ┌N   W   S┐  S   P   E   P   T
 TGT GAA CCA TTT GGA │AAC TGG TCA│TCT CCA GAA CCA ACC  850
                     └───────────┘
                 270                                 280
  C   Q   V   I   Q   C   E   P   L   S   A   P   D   L   G
 TGT CAA GTG ATT CAG TGT GAG CCT CTA TCA GCA CCA GAT TTG GGG
                                     290
  I   M  ┌N   C   S┐  H   P   L   A   S   F   S   F
 ATC ATG │AAC TGT AGC│CAT CCC CTG GCC AGC TTC AGC TTT  934
         └───────────┘
                 300
  T   S   A   C   T   F   I   C   S   E   G   T   E   L   I
 ACC TCT GCA TGT ACC TTC ATC TGC TCA GAA GGA ACT GAG TTA ATT
 310                                             320
  G   K   K   K   T   I   C   E   S   S   G   I   W
 GGG AAG AAG AAA ACC ATT TGT GAA TCA TCT GGA ATC TGG 1018
                             330
  S  ┌N   P   S┐  P   I   C   Q   K   L   D   K   S   F   S
 TCA │AAT CCT AGT│CCA ATA TGT CAA AAA TTG GAC AAA AGT TTC TCA
     └───────────┘
         340                                     350
  M   I   K   E   G   D   Y   N   P   L   F   I   P
 ATG ATT AAG GAG GGT GAT TAT AAC CCC CTC TTC ATT CCA 1102
```

FIG. 4B

```
           V   A   V   M   V   T   A   F   S   G   L   A   F   I   I
                                         360
          GTG GCA GTC ATG GTT ACT GCA TTC TCT GGG TTG GCA TTT ATC ATT
                             370
           W   L   A   R   R   L   K   K   G   K   K   S   K
          TGG CTG GCA AGG AGA TTA AAA AAA GGC AAG AAA TCC AAG        1186
                 380
           R   S   M   N   D   P   Y   *
          AGA AGT ATG AAT GAC CCA TAT TAA ATCGCCCTTG GTGAAAGAAA

ATTCTTGGAA TACTAAAAAT CATGAGATCC TTTAAATCCT TCCATGAAAC 1280
GTTTTGTGTG GTGGCACCTC CTACGTCAAA CATGAAGTGT GTTTCCTTCA
GTGCATCTGG AAGATTTCT ACCTGACCAA GAGTTCCTTC AGCTTCCATT 1380
TCACCCCTCA TTTATCCCTC AACCCCAGC CCACAGGTCT TTATACAGCT
CAGCTTTTTC TCTTTTCTGA GGAGAAACAA ATAACACCAT AAAGGGAAAG 1480
GATTCATGTG GAATATAAAG ATGGCTGACT TTGCTCTTTC TTGACTCTTG
TTTTCAGTTT CAATTCAGTG CTGTACTTGA TGACAGACAC TTCTAAATGA 1580
AGTGCAAATT TGATACATAT GTGAATATGG ACTCAGTTTT CTTGCAGATC
AAATTTCGCG TCGTCTTCTG TATACGTCCA GGTACACTCT ATGAAGTCAA 1680
AAGTCTACGC TCTCCTTTCT TTCTAACTCC AGTGAAGTAA TGGGGTCCTG
CTCAAGTTGA AAGAGTCCTA TTTGCACTGT AGCCTCGCCG TCTGTGAATT 1780
GGACCATCCT ATTTAACTGG CTTCAGCCTC CCCACCTTCT TCAGCCACCT
CTCTTTTTCA GTTGGCTGAC TTCCACACCT AGCATCTCAT GAGTGCCAAG 1880
CAAAAGGAGA GAAGAGAGAA ATAGCCTCCG CTGTTTTTA GTTTGGGGGT
TTTGCTGTTT CCTTTTATGA GACCCATTCC TATTTCTTAT AGTCAATGTT 1980
TCTTTTATCA CGATATTATT AGTAAGAAAA CATCACTGAA ATGCTAGCTG
CAACTGACAT CTCTTTGATG TCATATGGAA GAGTTAAAAC AGGTGGAGAA 2080
ATTCCTTGAT TCACAATGAA ATGCTCTCCT TTCCCCTGCC CCCAGACCTT
TTATCCACTT ACCTAGATTC TACATATTCT TTAAATTTCA TCTCAGGCCT 2180
CCCTCAACCC CACCACTTCT TTTATAACTA GTCCTTTACT AATCCAACCC
ATGATGAGCT CCTCTTCCTG GCTTCTTACT GAAAGGTTAC CCTGTAACAT 2280
GCAATTTTGC ATTTGAATAA AGCCTGCTTT TTAAGTGTTA AAAAgaattc 2330
```

FIG. 4C

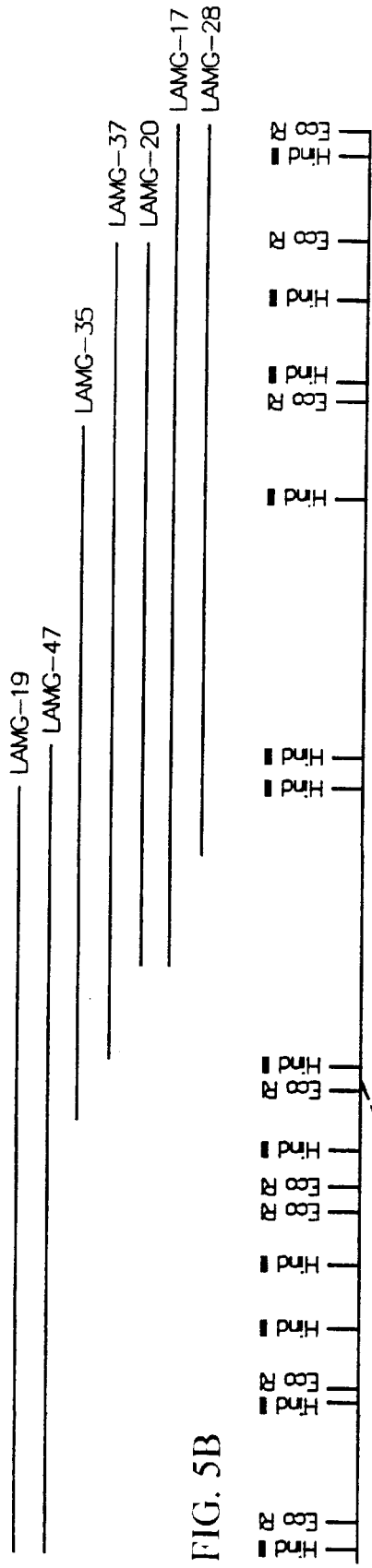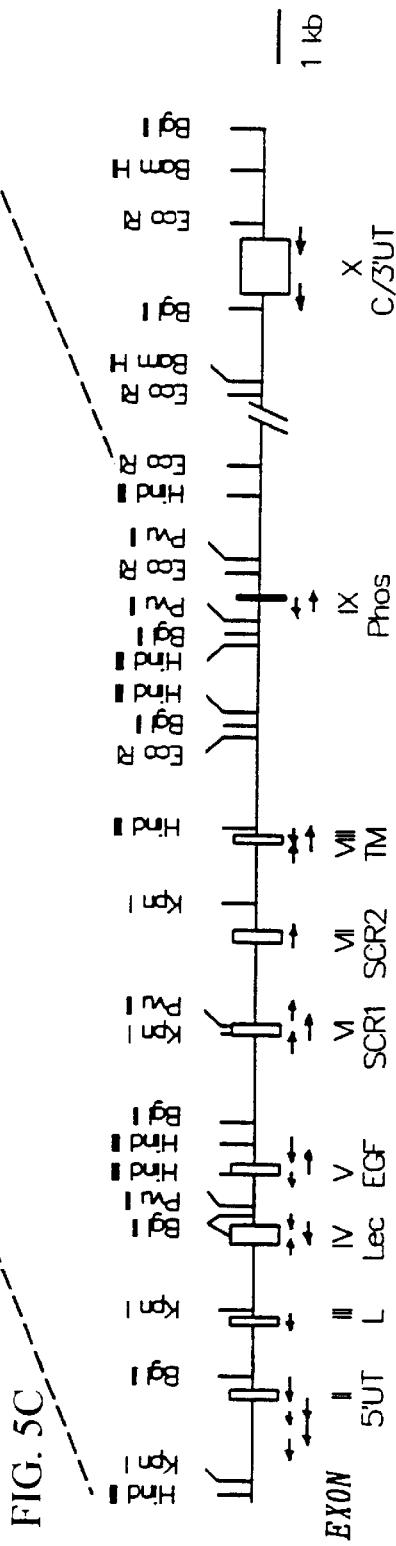
FIG. 5A
FIG. 5B
FIG. 5C

EXON II (5' Untranslated Region and Translation Initiation Site)
```
AGAGAGCTG TTATAAAGAT TAAACAATAT AATAAATATG GCGCGTGAGC TTCAGAGTTT TTGTTGTTGT TATTATTATT TTCCTAAAAA TGCAAATCTG ATTTGCATTT
GACTCATTGA CTCACATCAG TGGGTCTTCC TTTTTATTGT CCTTCATCAT ATGGGTCCTA ATTTCACATG CAGTCTTATA AAACCATCTC ATTTTATAGT CCAAGAATAT
TAAAGTACT TGTAGGCTC CAAACCTACA CGGTGAAAAG CTAGAGACA TGGGCTCTCT TCAGGGGTTA ACTTCAGGAA GTGCCACTAA CAAGGACGTC CACTAGGTGG
TGAGCAAGGA AAGACGGAGG GAAACGAGTC AAGTCCACTG CTTAGCTCTA CTGAAGTTTT GCAAACATCA TAAATATGTC TGAAATGCAG TTTTGATTTG
TAGTATTTGC AATTTCCAAG GGCCATTTAC CACAGGTAGC CAAGAGTTAG TTTTAGCATTT ATGAAAAAGA TAGGGAGGG TGGTGGTTAA GAAGGAGGTG GAGGAGAGAG
TGAAGGAGGA AGAGGAGAAC AAGAAGCAAA CAAAACCAAA AACAAGAACA AGTAGAAGAA GAGGAGCAGG GAGGAAGAA AAGAGGAAGA AGAACAGCAA CAACAATGAG
TGAAGGAGGA GGAGGGTAAG GAAAGATGCA TAGGAGAATG GAAGGAAGGA TAGAAAGGAG GGAAGGAAGA TCACATTACT TTCTGATCAG CAGTTCATTT
TTGTCTCAGT GGGAGGCAAT AGAGGCCAGT CTAGGAAAAG GGTGGGGAAA GAGGAAAAGA AAGTGCAGGA GCCCAAGGGG AGGAGGAGGA GGATGTGAGA
CTGGGTTAGA GAAATGAAAG AAGCAAGGC TTTCTGTTGA CATTCAGTGC AGTCTACCTG CAGCACAGCA CACTCCCTTT GGGCAAGGAC CTGAGACCCT TGTGCTAAGT
CAAGAGGCTC AATGGGCTGC AGAAGAACTA GAGAAGGACC AAGCAAAGCC ATG GTGAGCCTTT CAGCCCTAAAA GACGTTTAGA TGCTCAGATA GAAACTCTTG
GGGTTGTAGA GGCAGGTGGC AAGGATAGGA ATCACCCCAT TTCAATTCTG GTTTTAAATA ATATAGAAAC TAAACATTTT CTCAGACCCT CAAAAAAAGT
```

EXON III (Leader Domain)
```
CACTGAGA CTAAGCGTAA AATAAATAGA ACAAACAAAC TGTGCATCAG TTCTGCATAG TTCTGATGTA AATTTGAAGT AATTTTCATC TATGTCTGAG AAACCTGTTA CCTCAGACAG
GGTTAGTAGA CATATGTGTT TTATTCTGAT TATTAAGAAA GTTGTAAGCA CCACCTCAAA GGCTATAAAT GTGTGGTTTA AGGTATACA TCTAAATATA ATTTTGTATT
TCATTTGCAG ATA TTT CCA TGG AAA TGT CAG AGC AGG GAC TTA TGG AAC ATC TTC AAG TTG TGG GGG TGG ACA ATG CTC TGT
TGT G GTATGTTATG ATATTTATAT ATCACTAAGT CTATTTACT TATATTCATT TTT
```

FIG. 6A

```
EXON IV (Lectin Domain)
CT GGAGTAGTGC TAGTTCTTT TTAGCTGTAA CATTATGTAA GTCTCCATAG GTCACACTGA TGTCTTGCAG AT TTC CTG GCA CAT CAT GGA ACC GAC TGC
TGG ACT TAC CAT TAT TCT GAA AAA CCC ATG AAC TGG CAA AGG GCT AGA AGA TTC TGC CGA GAC AAT TAC ACA GAT TTA GTT GCC ATA
CAA AAC AAG GCG GAA ATT GAG TAT CTG GAG AAG ACT CTG CCT TTC AGT CCT TAC TAC TGG ATA GGA ATC CGG AAG ATA GGA GGA
ATA TGG ACG TGG GTG GGA ATC CTC ACT AAA TCT CTC ACT GAA GCA GAA GAT GGT GGA GAT GAG CCC AAC AAC AAG AAG AAC AAG
GAG GAC TGC TGC GTG GAG ATC TAT ATC AAG AGA AAC AAA AAG GAT GCA GGC AAC TGG AAC GAT GAC GCC TGC CAC AAA CTA AAG GCA GCC CTC
TGT TAC ACA G GTAGGGAGTG ACAAGACGGC TATGCTGCCT CAGACTCAGG AAGGGCCACG GTTAAGAGAA TACTTCAGATT TA EXON V (EGF Domain)
AAAATTTTAG CCATATGATT TTTATGCTAT GAATTTACCA AATAAACCTT TCCTGATTAT TTAAATCATC TCAGACAAAA GGTTATCTAT GTCTAAAGAA ATGACTTTGA
GTACTAAAAT GTAATCACAT TAAATATTT TTTTTCTGAC CTCCTAAAG CT TCT TGC CAG CCC TGG TCA TGC AGT GGC CAT GGA GAA TGT GTA
GAA ATC ATC AAT AAT TAC ACC TGC AAC TGT GAT GTG GGG TAC TAT GGG CCC CAG TGT CAG TTT G GTAAGTCTCT TTCCTTCTT
TGCTTCTTCT TAGGTAAAGT CACAGGAATC ATTATAGCTT ATCATGAAGC TGGTTGGAAC AAAATGATAC TAGCCACTCT GAGAAATGGG AAGTTTTGAT CAGAAAGCTC
TGCTTTCACA ATATTGTTAC CTTTCCGTAA AGATTTCATA AGTCAGCATG AAGTTTCGAT TCACTTCTCA ACAAGTCTTT TTGAGTACCA CAAGAAGCAC AGTGTTGGGA
TAAAGCTGTC AGGGTACAA TAAGGAATTA GCATGGTAGA TTCCCGCTCT CAAGAAGCTC ACGATCTAAT GAGCTTGTTA GATTAATTAG AACTCTAAGG TCTGGAAGAA
ACTATGCCAT TTATCATTAG GAGGCTGAGT TACCCAGAAA GTATCTTGCT TTTTCCTTCT AGTAGTTCCT TCCTTCTTG CAGTTCTCCA CACTTAACAC ATGTGCTCTG
TAGCACACTG ACTTTGCTGG TGGCCTTCTC TCTCATTTTG CACATGGCCA TCTCATTTTAAG ACATTGTTCA AAGACAGTTT CTTCTAGGAA GCTT EXON VI (SCR I Domain)
CTCTGA TGTGATAGTT ATTTCCCGAC TAAGCTGGTC ATTCCCAGTT ACACCTATTT GGCTTTAAGG ATTCTCACTA CAGATAATAC TGAAGATAAT AATATGAAGA
CTAGTAATG TTTACTTAGA ATTTCTGATG AGTCAGGCTT TGTTCTAACG TCCTTGACTT ATGCTAATTG AATTACATTT AGTTTCCATA TCAATTGAT AAAGATAACA
CAATTTCATT ATTCCTCTA TATAGATGAA GAAACTGAAG TTGGAGGGT CAAGAACCT TGTTTAAAGG CACATGGTTA TCAAGTGGCA GGGCTAGGAT TCAAATCCAG
GCGTCAGTTC CTCTTAACTC TTCCCCATAC TGTTTCTTTC CCTATTGAAG TG ATT CAG TGT GAG CCT TTG GAG GCC CCA GAG CTG GGT ACC ATG GAC
TGT ACT CAC CCT TTG GGA AAC TTT GCC TTC AGC TTC AGC TCA CAG TGT GCC TTC AGC TGC TCT GAA GGA ACA AAC TTA ACT GGG ATT GAA
GAA ACC ACC ACC TGT GGA CCA TTT GGA AAC TGG TCA TCT CCA GAA CCA ACC TGT CAA G GTGAGTAACT TCAGACTAGA GGTTTTGTCA TGCAATCCTG
GGCTTACAGT CAGAACATTC AGTAGAAGTT TGCTAGAGAAG TCAAACTTAG GATCCTAATT TAACCTAACT TTTGTTTAAC CTACTGTGAT GTTTCTCAAA GGACTTATTC
```

FIG. 6B

```
EXON VII (SCR II Domain)
GAGGTCAC CTTAGCTAGG GCAGCAGCCT GGAGTAGCTA CTCCTCTCCC CACAGCTTTC AATGCTTCCT TGCCTTCATC TCTCATTCAC CACCCACCAT CATTCTCAAG
AAATAAAGC CTGGAAGCAA TATCACAAGT AATGTAGTCA GCCAGCTTTG GCTAAAAATC CAAAGCTCAA GGGAGGGTCT CTACTCAGAA ATACTGTTTT GTCTTTTTTT
TTTTTCTTT TTCATTGAAG TG ATT CAG TGT GAG CCT CTA TCA GCA CCA GAT TTG GGG ATC ATG AAC TGT AGC CAT CCC CTG GCC AGC
TTC AGC TTT ACC TCT GCA TGT ACC TTC ATC TGC TCA GAA GGA ACT GAG TTA ATT GGG AAG AAG AAA ACC ATT TGT GAA TCA TCT
GGA ATC TGG TCA AAT CCT AGT CCA ATA TGT CAA A GTGAGTAAGT TTGTCCTGGA ACTGAA EXON VIII (Transmembrane Domain)
TATCAGAAC TAAGAAAGCT TGGGCTGCAG GTCGACTCTA GGTGCATTTT CAGGAACTCT ATGAACCACA AATCTGGGCA TTGAGATTCT GTAGGCATTA GACTAGCAAG
GCTGGTCAGT CTTTGCCTAT GCTGTAGACT CATCAGGGGC CTTCCCATGC CAGTTTCCTC ATCTGTCAAA TGGCATCATT TGGGCTACTA CTGGGAGATG TAAGGAGAA
AAAGTCAAA TATCATGAGA TAGACTAAGG AAATAATGCT GGTGGTCTCA TGCTATGTGC CTTACTGATT TCTCTTTCAG AA TTG GAC AAA AGT TTC TCA ATG
ATT AAG GAG AGT GAT TAT AAC CCC CTC TTC ATT CCA GTG GCA GTC ATG GTT ACT GCA TTC TCT GGG TTG GCA TTT ATC ATT TGG CTG
GCA AGG AGA TTA AAA AAA G GTATGTGAGT TTAACTTCAC ATGAAAAGAA CACAACTTTA AAGTGAAAAA GAAAAAAAAA AGAAACCCAC AGGAAATTAA
ATGTGATAGA TTCAACACAA GCAAGGATGCC AAGCTT EXON IX (Phosphorylation Domain)
TAGTTTACA GTATTAGCAG CTGTCCCTCA AGGAAGAATC TGCAGGTAGA TGAGATGCAG ATTGGGTGGG ATAAACACTT GAATGACATA TTGGGTCTTG CCACCAGGCA
ATTTACAAT TCTGTCTTCT TGAGTAGCAC TGAGTAGCCA TGGAACCTCA GGAGCCATCT GCATCAACAT GTCTGTTCTG TATTAGTGTC TACCACTCTT TATTAAGCCA
GTTCCTCAAA TCTCCTTTGA CACAGATAGG GTCCACCTAA CAAATACCTA ATATACTTCA AAAGACAGTT TTGAGAGTGG GAGTCTTCCT TCTCCCTTAC TTGAAAAACT
TTAAATTGTC TAATTTTTGC TAATGCCTTT TTCTCTATTT TCTATTTCAG GC AAG AAA TCC AAG AGA AG GTAAGTTTTA TTAGTGGCGA GGAGTTTCCA
CATCTGCTGA TTCATTCTCT ACTTCTTAAG TTACTTCTGC TCTAGCTAGA CACATACCCA TAGTAGTTAT TACTGGGTCT ATCAATGACA GATAGG EXON X (Cytoplasmic Tail and 3' Untranslated Region)
ATAAGCATC ACTAAAGAGC TTGTTAGGGG TGCAGAATCT CAGGCTCCAC TCAGACCTAC TGAATCAGAG AGCCTGGCCT TCTGTCATTTT AACACCATCT CTGAGTGGTA AGgACATGAA
AATCTGAGAA GTGCTGCTAC TAGGGTTTGC TTACATTTGT TCATCTTCAG AGGTTCCTAA AGCCTGGCCT CTTGTCTGAG ATTTCCAGCT CCTTGCTCCT
CTTCTCATCT CTAATGAATA TTTACCTTTA CTACTAACAC TCCAAGTTTT GCAATTTGTA AACTCTTATT ATCTTTTGTT TTTCTTTCAG T ATG AAT GAC CCA
TAT TAA ATCGCCCTTG GTGAAGAAA ATTCTTGGAA TACTAAAAAT CATGAGATCC TTTAAATCCT CCATGAAAC GTTTTGTGTG GTGGCAC(983 BASES1G
CAATTTTGCA TTTGAATAAA GCCTGCTTTT TAAGTGTTAA CTAGTTTGCC TAGTTTGTTA TTTTGAAAAT TGATCATATG TTTTGTTTTC TCCCCAGTGA GTTACATGCT
TAAGTTTCAG CATCCCTCTT TCTCTATGGC ATCTGATGAC CTGGGTCAGA TATCACCTAA TGTCAACAGC TGAATTC
```

FIG. 6C

FIG. 7A    LECTIN DOMAINS

```
                         *                                                    #
human-L:  WTYHYSEKPMNWQRARRFCRDNYTDLVAIQNKAEIEYLEKTLPFSRSYYWIGIRKIGGIW
mouse-L:  ---------------EN--K--KQ--N-------R------N----K-PY-------KM-
rat-L:    ---------------RS--EN--KF-KH------R--------------KNPT----KT-
bovine-L: ---------------KR--P-EK--A---E--------G-----N--Q----T----VE-V
human-E:  ---------------S-NT-TEA-TYDE-SAY-QQR--H-------E----NSI-SY-P---VNNV-
mouse-E:  ---------------S--A-TEM-TFEE--DY-QKT--A-----QE----NS-FSY-P---N-T-
bovine-E: ---------------T-AYS-NIS-KY-QNR--------------------D--V--YYS---NNKT-
human-P:  ---------------N--T-AYS-NNS-V---RHF-----------N--AH-NDVI--FN---NNK-
mouse-P:  ---------------N-TYS-NYS-A---QKY--K-----------N--A--NE-I-YYN---NNK-

#     #           #        * #  # ###  *
human-L:  TWVGTNKSLTEEAENWGDGEPNNKKNKEDCVEIYIKRNKDAGKWNDDACHKLKAALCYT
mouse-L:  ------T--K----A-----------S-------ER-S------R-------------
rat-L:    ------T--K-----------------------ER-S------R-------------
bovine-L: ---------------K--A--------R-S-----------S-----A-T-------
human-E:  V----Q-P-----K--AP-----RQKD------E--V-M----ER-S-K-L------
bovine-E: --I-----K--T-AP-------QSD--------E--S-----EK-T-Q-L----K
human-P:  ------K-A--N------A-N-----R-N------------SPSAP-----EH-L-K-H---
mouse-P:  ------T------------A-N-----NQ------------S-SAP-----EP-F-R-R---
bovine-P: ------K-T-----------A-N------R-NQ--------SLSAP-----EP-W-R-R----R
```

FIG. 7B    EGF DOMAINS

```
              *        *          *                 *
human-L:  ASCQPWSCSGHGECVEIINNYTCNCDVGYYGPQCQF
mouse-L:  -----G--N-R----T--H--I--A-------Y
rat-L:    -----E--NR----T--N--I--P--------Y
bovine-L: ---K--------Q--V-------L----E---- human-E:  -A-TNT---------------T------K--P-FS-LK-EQ
mouse-E:  -TNA-----------I-T--S---K-HP-FL--N-EQ
bovine-E: -A-N-TP-G-----------------Q-HP-FK-LK-EQ human-P:  -----DM---KQ---L-T-G----S-YP-F----E-EY
mouse-P:  -----DM---NQ-K-I-T-GS---S-YP-F----E-EY
bovine-P: -----DM---KQ---I-T-G----S-YP-F----E-EY
```

USE OF CHIMERIC SELECTINS AS SIMULTANEOUS BLOCKING AGENTS FOR COMPONENT SELECTIN FUNCTION

RELATED APPLICATIONS

This application is a division of United States application Ser. No. 08/340,539, filed Nov. 16, 1994, which is a continuation of United States application Ser. No. 08/008,459, filed Jan. 25, 1993, now abandoned which is a continuation-in-part of Tedder, U.S. patent application Ser. No. 07/983,606, filed Nov. 30, 1992, which is a continuation under 37 CFR 1.62 of Ser. No. 07/730,503, filed Jul. 8, 1991, and Ser. No. 07/313,109, filed Feb. 21, 1989, both now abandoned and a continuation-in-part of Tedder, U.S. patent application Ser. No. 07/700,773, filed May 15, 1991 now abandoned; of Tedder, and a CIP of application Ser. No. 07/737,092, filed Jul. 29, 1991 now abandoned; of Tedder et al., U.S. patent application Ser. No. 07/770,608, filed Oct. 3, 1991 now abandoned; and of Tedder et al., U.S. patent application Ser. No. 07/862,483, filed Apr. 2, 1992 now U.S. Pat. No. 5,389,520, the whole of which are hereby incorporated by reference herein.

GOVERNMENT RIGHTS

Part of the work leading to this invention was made with United States Government funds. Therefore, the U.S. Government has certain rights in this invention.

FIELD OF THE INVENTION

This invention relates to the selectin family of receptor adhesion molecules and particularly to agents interfering with selectin function.

BACKGROUND OF THE INVENTION

The ability of leukocytes to leave the circulation and to migrate into tissues is a critical feature of the immune response. Normally, the infiltrating leukocytes phagocytize invading organisms or dead or damaged cells. However, in pathologic inflammation, infiltrating leukocytes can cause serious and sometimes deadly damage. Leukocyte-mediated inflammation is implicated in a number of human clinical manifestations, including the adult respiratory distress syndrome, multi-organ failure and reperfusion injury.

The selectin family of receptor adhesion molecules mediates the initial interactions of leukocytes with endothelium (Springer, Nature 346:425–434 (1990); Lasky, Science 258:964–969 (1992)). L-selectin (also known as LAM-1) is expressed on the surface of most classes of leukocytes (Griffin et al., J. Immunol. 145:576–584 (1990); Tedder et al., J. Immunol. 144:532–540 (1990)) and mediates the binding of lymphocytes to high endothelial venules (HEV) of lymph nodes and to activated endothelium. P-selectin (also called PADGEM, CD62 or GMP-140) is expressed by activated platelets and endothelial cells (Johnston et al., Cell 56:1033 (1989); Hsu-Lin et al., J. Biol. Chem. 259:9121 (1984)) and mediates adhesion between myeloid cells and activated endothelium or activated platelets (Gallatin et al, Nature 304:30–34 (1983); Spertini et al, J. Immunol. 147:2565–2573 (1991); Larsen et al, Cell 59:305–312 (1989); Geng et al, Nature 343:757–760 (1990)). Another member of the family E-selectin (also known as ELAM-1) is expressed by activated endothelial cells (Bevilacqua et al., Science 243:1160 (1989); Bevilacqua et al., Proc. Nat'l Acad. Sci. USA 84:9238 (1987)) and partially mediates the binding of neutrophils to endothelium at sites of inflammation (Bevilacqua et al., Proc. Nat'l Acad. Sci. USA 84:9238 (1987)). All selectins are derived from evolutionarily related genes (Collins et al., J. Biol. Chem. 266:2466–2478 (1991); Johnston et al., J. Biol. Chem. 34:21381–21385 (1990); Ord et al., J. Biol. Chem. 265:7760–7767 (1990); Watson et al., J. Exp. Med. 172:263–272 (1990)), and are characterized by an $NH_2$-terminal, $Ca^+$-dependent lectin domain, an epidermal growth factor (EGF)-like domain followed by multiple short consensus repeat (SCR) domains, a transmembrane region, and a cytoplasmic tail. Although the lectin domains are critical for the binding of specific carbohydrate ligands (Springer, Nature 346:425–434 (1990); Lasky, Science 258:964–969 (1992)), the role of the conserved EGF-like domains is unknown.

It has been proposed that the treatment of a patient suffering from pathologic inflammation with an antagonist to adhesion receptor function can result in the reduction of leukocyte migration to a level manageable by the target endothelial cells and the subsequent dramatic recovery of the patient. Local administration of therapeutic agents can block competitively the adhesive interactions between leukocytes and the endothelium adjacent to an inflamed region. Therapeutic agents can also be administered on a systemic level for the treatment of a patient suffering from disseminated inflammation (Harlan and Liu, eds., *Adhesion: Its Role in Inflammatory Disease*, W. H. Freeman (in press))

SUMMARY OF THE INVENTION

We report here that the EGF-like domains of P-selectin and of E-selectin can participate directly in cell adhesion, having ligand binding sites distinct from those of their respective lectin domains. Cell adhesion mediated at least by the P and E-selectins may be complex, involving interactions between the lectin domain and a carbohydrate ligand, and separately, between the EGF-like domain and one or more proteins or other ligands. Our discovery of a difference in at least one of the ligands recognized by the lectin and EGF domains of a given selectin has permitted the preparation of chimeric polypeptides that combine within one molecule the ability to target two or more different selectin ligands and the use of these agents in therapy or in the preparation of additional classes of antagonists to selectin function.

Thus, the invention generally features chimeric peptides or polypeptides that combine ligand binding portions from within the lectin and EGF domains of two different selectins. The peptides or polypeptides can be composed solely of the indicated portions of lectin or EGF domains or they can include portions of any of the remaining domains (SCR, transmembrane or cytoplasmic), or the entire extracellular portion, of a generic selectin molecule. The peptides or polypeptides also can be joined to a carrier protein (e.g., a soluble portion of an immunoglobulin molecule) to increase the serum half-life of the therapeutic agent. In another aspect, the invention features nucleic acid encoding the chimeric polypeptides.

The chimeric polypeptides can be used as therapeutic agents to antagonize selectin function. They are also useful for screening for agents that are simultaneously antagonists of the function of lectin and EGF domains of different selectins.

As used herein, the term "polypeptide" is intended to include shorter molecules, or "peptides." The term "essentially purified" refers to a polypeptide sequence that has been separated or isolated from the environment in which it was prepared or in which it naturally occurs.

BRIEF DESCRIPTION OF THE DRAWINGS

Other features and advantages of the invention will be apparent from the following description of the preferred embodiments thereof, taken in conjunction with the accompanying drawings in which:

FIG. 1 shows the structure and expression of L-selectin/P-selectin chimeric proteins (Lectin, lectin domain; EGF, epidermal growth factor-like domain; SCR, short consensus repeat; TM, transmembrane domain; C, cytoplasmic domain);

FIG. 2A: natural P-selectin;

FIGS. 4A–4C show the cDNA nucleotide sequence (SEQ ID NO: 1) encoding L-selectin and also show the amino acid sequence of L-selectin (SEQ ID NO: 2);

FIG. 5A shows the location relative to a restriction enzyme map of the lyam-1 gene of the overlapping genomic fragments from seven clones containing inserts that hybridized with LAM-1 cDNA probes. FIG. 5B is a restriction enzyme map of the lyam-1 gene. FIG. 5C shows the exon-intron organization of the lyam-1 gene.

FIGS. 6A, 6B and 6C show the nucleotide sequence of exons II through X of the lyam-1 gene (SEQ ID NOS: 3–11).

FIGS. 7A and 7B show the homology among the L-selectin lectin domains (SEQ ID NO: 5) and the lectin domains of P- and E-selectin, respectively, and among the L-selectin EGF domain (SEQ ID NO: 6) and the EGF domains of P- and E-selectin, respectively.

DESCRIPTION OF THE PREFERRED EMBODIMENTS

Figures 2A, 2B, 2C, 2D:
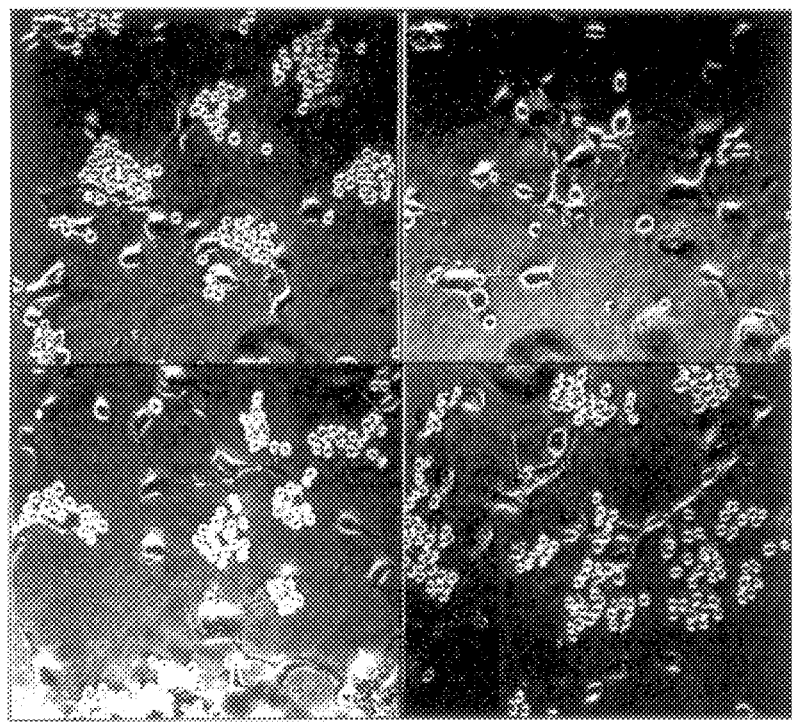
FIG. 2a (two panels) shows binding of HL-60 cells to COS cells transfected with natural and chimeric selectins.
FIG. 2B: natural L-selectin.
FIG. 2C: chimeric selectin P2L.
FIG. 2D: chimeric selectin L2P.

We have examined the role of the lectin and EGF-like domains of the L-, P-, and E-selectins in cell adhesion and have determined that the EGF-like domains of P- and E-selectin play a direct role in ligand recognition and leukocyte adhesion mediated by the respective selectin. This discovery has permitted the preparation of chimeric polypeptides that combine within one therapeutic agent the ability to target two or more different selectin ligands and the use of these agents in therapy or in the preparation of additional classes of antagonists to selectin function.

Determination of the binding specificity of selectin lectin and EG-F domains

The functional activities of the lectin and EGF-like domains of L-, P-, and E-selectin in the adhesive events described above were examined using a panel of L-selectin/P-selectin and L-selectin/E-selectin chimeric molecules. Referring to FIG. 1, these hybrid polypeptides were created by exchange of cDNA encoding the lectin, EGF, or both lectin and EGF domains of the desired selectin and expression of the chimeric nucleic acid, as described in the Experimental Procedures section. Many other methods familiar to those of skill in the art can be employed to prepare similar products.

The chimeras conserve the overall polypeptide backbone structure of the selectins, and resulted in minimal changes in the junctions between domains. The functional characterization of these chimeric selectins therefore offered a powerful approach to determining the molecular basis of cell adhesion mediated by these molecules and to preparing diagnostic and therapeutic agents incorporating properties of individual selectins into the same polypeptide.

Expression of the chimeric proteins in COS cells was verified and quantitated using panels of P-, E- and L-selectin domain-specific monoclonal antibodies (mAb) in direct adhesion assays. The chimeric cDNA were subcloned into the pMT-2 vector and used to transiently transfect COS cells as described under Experimental Procedures. Twenty-four hours before analysis, $2.5 \times 10^4$ transfected COS cells were replated into 96 well plates. Expression of domain-specific epitopes by chimeric selectins was assessed using mAb reactive with specific domains and a surface immunofluorescence assay as described (Luscinskas et al, J. Immunol. 149:2163–2171 (1992)).

Referring again to FIG. 1, the individual constructs, containing the indicated domains of P-selectin and L-selectin, reacts only with anti-L-selectin and anti-P-selectin monoclonal antibodies recognizing the specific, indicated domains. These results demonstrate that the chimeric cDNA encoded the expected proteins and that each protein was expressed and readily detected on the surface of COS cells. Note that the LAM1-1 mAb fails to recognize either the L2P or P2L proteins, and therefore defines an epitope composed of residues in both the lectin and EGF domains. Values given are means of absolute optical density (OD) units from which OD units obtained with a control non-binding mAb were subtracted. Experimental values less than the control values are represented as zero. The values presented are typical of those obtained in three experiments. The standard deviations for these fluorescence measurements were less than 15%.

Characterization of the adhesion reactions mediated by the selectin lectin and EGF domains The HL-60 myelomonocytic cell line expresses ligands for P-selectin (Larsen et al, Cell 59:305–312 (1989); Geng et al, Nature 343:757–760 (1990)) and E-selectin (Bevilacqua et al., Science 243:1160 (1989); Bevilacqua et al., Proc. Nat'l Acad. Sci. USA 84:9238 (1987)) and was therefore used to assess P-selectin and E-selectin function. Referring to FIGS. 2A–2D, HL-60 cells bound at high levels to COS cells expressing P-selectin, but did not bind to COS cells expressing L-selectin. HL-60 cells also bound to COS cells expressing the chimeric protein P2L, in which the lectin domain from P-selectin was substituted for the lectin domain of L-selectin. Therefore, the lectin domain of P-selectin alone, when attached to the EGF-like and other domains from L-selectin, was sufficient to mediate high levels of HL-60 cell adhesion. However, the lectin domain of P-selectin alone was not solely responsible for all HL-60 binding, because HL-60 cells also bound to COS cells expressing L2P, in which the P-selectin lectin domain was replaced with that of L-selectin.

Figure 2E:
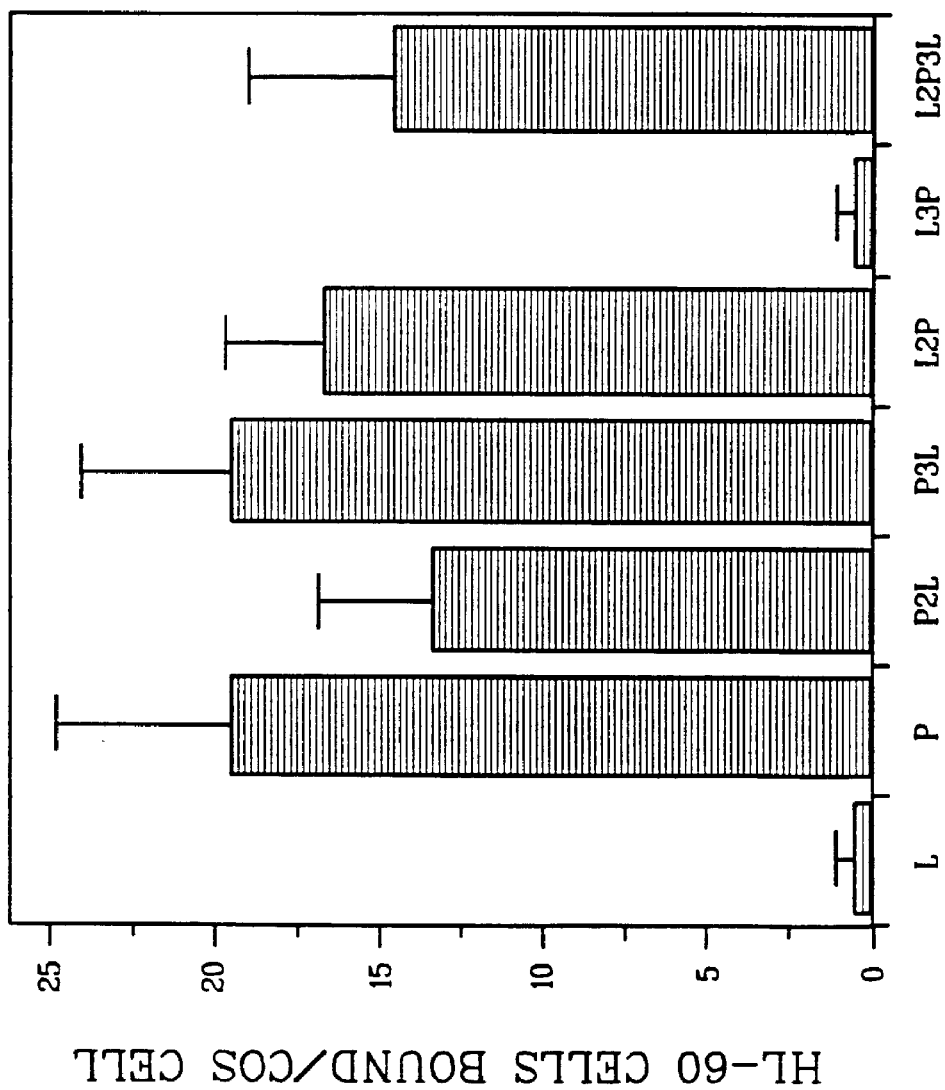
FIG. 2E shows mapping of the domain(s) of L2P responsible for adhesion of HL-60 cells (bars represent the means ±SD, and are representative of at least six experiments)

The domain(s) within L2P responsible for HL-60 adhesion were mapped using additional chimeric selectins. Referring to FIG. 2E, HL-60 cells bound to COS cells expressing L2P3L, which contains only the EGF domain from P-selectin, but did not bind to COS cells expressing L3P, which lacks both the lectin and EGF-like domains of P-selectin but contains the P-selectin SCR domains. Furthermore, binding of HL-60 cells to P3L, which contains both the lectin and EGF domains from P-selectin, was approximately equivalent to that of native P-selectin and significantly ($P<0.01$; Student's T test) higher than binding of cells to P2L, even though expression of P2L and P3L were approximately equal. These data indicate that both the lectin and EGF-like domains of P-selectin contain ligand binding sites capable of independently mediating HL-60 cell adhesion.

For study of ligand binding sites in E-selectin, four L-selectin/E-selectin chimeric molecules were constructed. L2E has the lectin of L-selectin and the remainder of E-selectin; E2L is the precise converse. LSE has the amino terminal 88 amino acids of L-selectin (i.e., 74% of the lectin domain) and ESL is the precise converse. Binding of HL-60 cells to COS cells expressing these chimeras was assessed as before. The constructs containing only a portion of a specific lectin domain exhibited zero binding, while the binding to chimeras containing lectin and EGF domains from different selectins was reduced by about a half. Therefore, the overall pattern of binding was similar to the results with L-selectin/P-selectin chimeras.

Determination of the influence of EGF-domains on the adhesive activity or specificity of the lectin domains Adhesion mediated by P-selectin involves sialic acid-bearing carbohydrates, possibly including the sLe$^x$ and/or related structures, as well as protein determinants (Larsen et al, Cell 63:467–474 (1990); Zhou et al, J. Cell Biol. 115:557–564 (1991); Moore et al, J. Cell. Biol. 118:445–456 (1992); Moore et al, J. Cell Biol. 112:491–499 (1991); Polley et al, Proc. Natl. Acad. Sci. USA 88:6224–6228 (1991); Larsen et al, J. Biol. Chem. 267:11104–11110 (1992) ). Therefore, the effects of neuraminidase and protease treatment of HL-60 cells on binding to COS cells expressing either P-selectin, P3L, or P2L was examined.

Figure 3A:
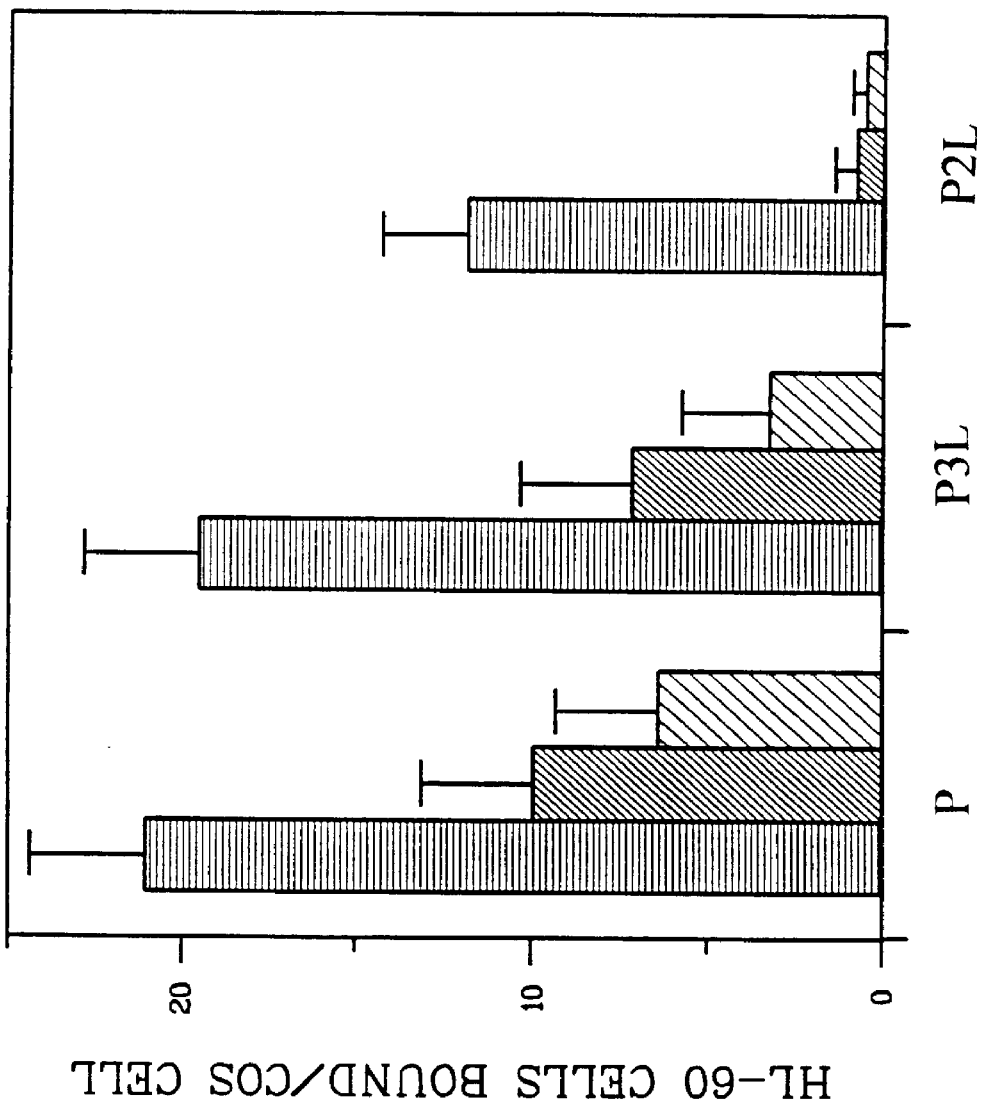
FIG. 3A shows neuraminidase sensitivity for adhesion mediated by the lectin and EGF domains of P-selectin. Horizontal hatching: untreated cells; tight diagonal hatching: neuraminidase treated cells; open diagonal hatching: cells pretreated with G1 mAb.

Removal of sialic acid residues from HL-60 cells significantly ($P<0.01$) but incompletely reduced adhesion of HL-60 cells to COS cells expressing native P-selectin or P3L (FIG. 3A). In contrast, removal of sialic acid residues from HL-60 cells nearly completely eliminated adhesion of HL-60 cells to P2L (FIG. 3A). In addition, binding to the E-selectin/L-selectin construct E2L was partially inhibited by pretreatment of the HL-60 cells with CSLEX1 mAb directed against sLex. Similarly, pretreatment of COS cells with mAb directed against the lectin domain of P-selectin significantly ($P<0.005$), but only partially, inhibited the adhesion of HL-60 cells to P-selectin or P3L, but abolished adhesion to P2L (FIG. 3A).

Figure 3B:
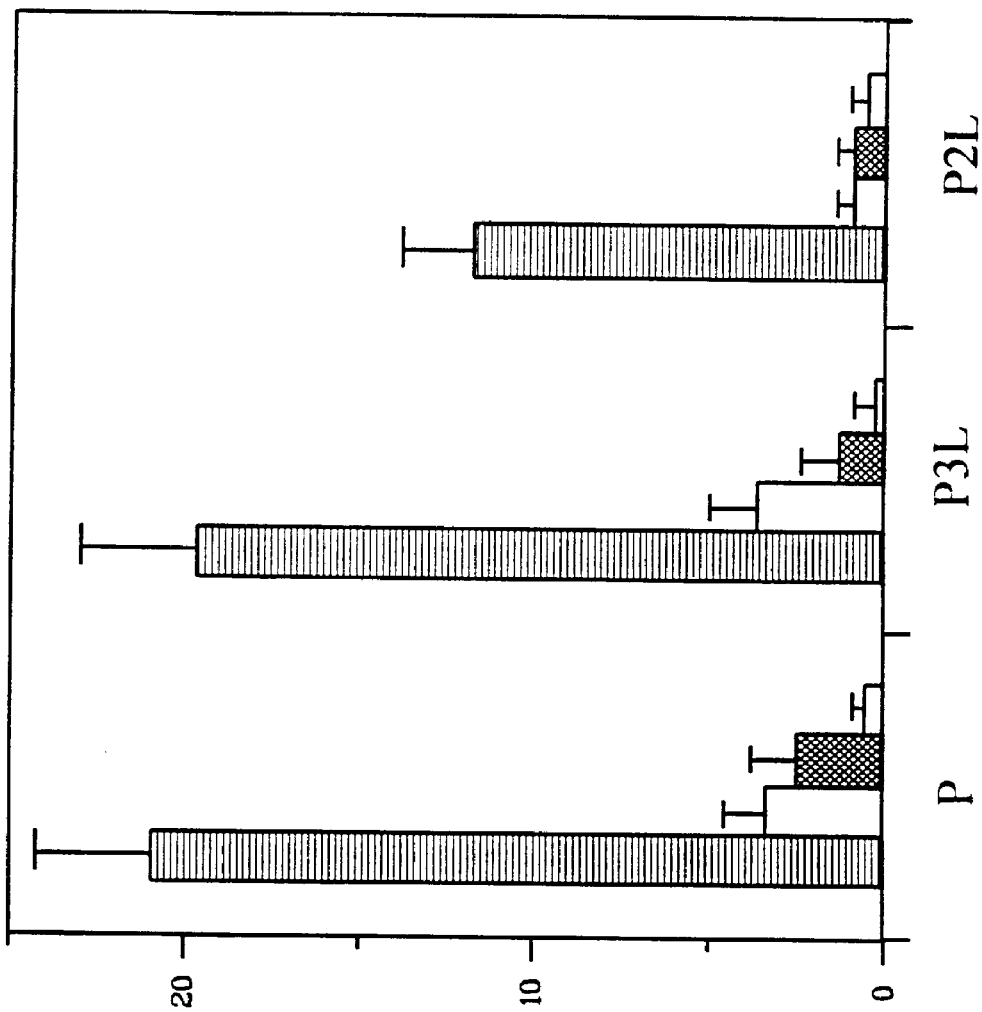
FIG. 3B shows protease sensitivity and $Ca^{2+}$ requirement for adhesion mediated by the lectin and EGF domains of P-selectin. Horizontal hatching: untreated cells; open: chymotrypsin treated cells; cross-hatching: papain treated cells; open: cells treated with 25 mM EDTA.

Treatment of HL-60 cells with either chymotrypsin or papain eliminated >90% of binding to COS cells expressing P-selectin, P3L, or P2L (FIG. 3B). In addition, 2.5 mM EGTA abolished adhesion (FIG. 3B). These results confirm the importance of the lectin domain in adhesion, and offer independent evidence that the EGF domain of P-selectin also plays a direct role in adhesion, recognizing a protein ligand.

Figure 3C:
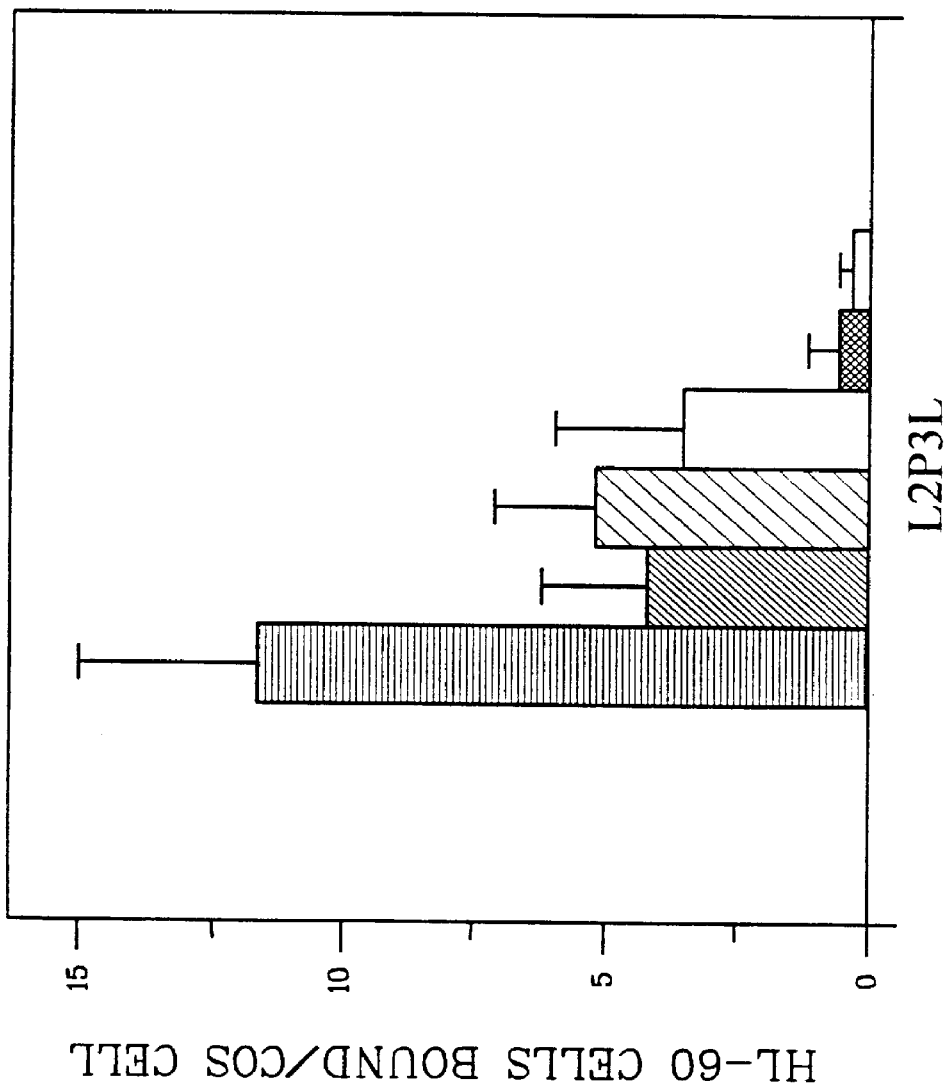
FIG. 3C shows an analysis of the binding of the chimera L2P3L. Horizontal hatching: untreated cells; close diagonal hatching: neuraminidase treated cells; open diagonal hatching: cells pretreated with LAM1-3 mAb; open: chymotrypsin treated cells; cross-hatching: papain treated cells; open: cells treated with 25 mM EDTA.

A similar analysis was performed on L2P3L to characterize adhesion mediated by the EGF-like domain of P-selectin. Adhesion of HL-60 cells to COS cells expressing L2P3L was also reduced, but not eliminated, by neuraminidase treatment of the HL-60 cells (FIG. 3C). MAb directed against the L-selectin lectin domain present within L2P3L also significantly ($P<0.01$) inhibited adhesion. These results suggest that recognition of specific carbohydrate structures on HL-60 cells by the lectin domain of L-selectin, which alone was not sufficient for cell adhesion, contributes to leukocyte adhesion in this system when this interaction is supported by the adhesive activity mediated by the EGF domain of P-selectin. Consistent with this hypothesis, rare (~1 plate) rosettes of HL-60 cells were occasionally observed on COS cells transfected with L-selectin (data not shown), and a soluble L-selectin/IgG fusion protein has a measurable affinity for purified, immobilized sLe$^x$ (Foxall et al, J. Cell Biol. 117:895–902 (1992)). Adhesion of HL-60 cells to L2P3L was eliminated by EGTA, indicating that adhesion mediated by the EGF-like domain is also Ca$^{2+}$-dependent, and was significantly ($P<0.01$) reduced by protease treatment (FIG. 3C).

Determination of the influence of EGF domains on the adhesive activity or specificity of the lectin domains In order to determine if the EGF-like domains of selectins have any influence on the adhesive activity or specificity of the lectin domain, stable transfectants of the 300.19 murine pre-B cell line expressing L-selectin, P-selectin, L2P or L2P3L were generated. These cells were tested for binding to lymph node HEV using the standard in vitro frozen section assay (Stamper Jr. et al, J. Exp. Med. 144:828–833 (1976)). Transfectants expressing P-selectin did not bind to HEV, whereas transfectants expressing L-selectin, L2P or L2P3L bound to HEV equivalently and at high levels (Table I).

TABLE I

Adhesion of cell lines to lymph node HEV is mediated by the lecitin domain of L-selectin.

| cDNA | LAM1-3 mAb | expt 1 | expt 2 | expt 3 |
|---|---|---|---|---|
| none | − | 0.047 ±0.02 | 0.12 ± 0.025 | <0.01 |
|  | + | <0.01 | ND | ND |
| L-selection | − | 3.43 ± 0.42 | 6.85 ± 0.45 | 2.44 ± 0.51 |
|  | + | 0.05 ± 0.2 | ND | <0.01 |
| L2P | − | 3.71 ± 0.26 | 6.64 ± 0.43 | 4.40 ± 0.3 |
|  | + | 0.074 ± 0.03 | ND | <0.01 |
| L2P3L | − | 5.71 ± 0.33 | 6.85 ± 0.18 | 3.94 ± 0.27 |
|  | + | 0.08 ± 0.03 | ND | <0.01 |
| P-selection | − | <0.01 | <0.01 | ND |

The lectin domain of L-selectin alone was therefore capable of mediating binding to HEV when attached to the EGF-like and other domains of P-selectin. The L2P and L2P3L chimeric selectins can therefore bind to different types of cells which express ligand(s) for either L- or P-selectin, reflecting the specificities of both of the parent selectins from which they are constructed. This acquisition of novel adhesive properties as a result of the exchange of lectin or EGF-like domains between selectins reinforces our hypothesis that the EGF-like domain of P-selectin can mediate cell adhesion. In addition, these data directly demonstrate the functional independence of the lectin and EGF-like domains, and therefore argue against a role for the EGF-like domain in determining the carbohydrate specificity of the lectin domain.

Structure of the L-selectin gene

As disclosed in U.S. patent application Ser. No. 07/983,606, cDNA encoding L-selectin has been cloned and the sequence determined, as shown in FIGS. 4A, 4B and 4C (SEQ ID NO: 1). The cDNA encodes a protein of 372 amino acids (SEQ ID NO: 2).

The structure of the lyam-1 gene, which encodes the LAM-1 protein, was determined by isolating overlapping genomic DNA clones that hybridized with a LAM-1 cDNA probe. The lyam-1 gene spans greater than 30 kb of DNA and is composed of at least 10 exons. The 5' end of the LAM-1 mRNA was mapped by primer extension analysis, revealing a single initiation region for transcription. Exons II through X contain translated sequences; exon II (SEQ ID NO: 3) encodes the translation initiation codon, residue 14 shown in FIG. 4B; exon III (SEQ ID NO: 4) encodes the leader peptide domain, residues 15–41; exon IV (SEQ ID NO: 5) encodes the lectin-like domain, residues 42–170; exon V (SEQ ID NO: 6) encodes the epidermal growth factor-like domain, residues 171–206; exons VI (SEQ ID NO: 7) and VII (SEQ ID NO: 8) encode the short consensus repeat unit domains, residues 207–269 and 270–331; exon VIII (SEQ ID NO: 9) encodes the transmembrane region, residues 332–373; exon IX (SEQ ID NO: 10) encodes seven amino acids containing a potential phosphorylation site, residues 374–380; and exon X (SEQ ID NO: 11) encodes the five remaining amino acids of the cytoplasmic tail and the long 3' untranslated region.

The pLAM-1 cDNA was labeled with $^{32}P$ and used as a probe to isolate hybridizing DNAs from a human leukocyte genomic DNA library. Approximately $1 \times 10^6$ plaques were screened, and 13 plaques that hybridized with the cDNA probe were identified and isolated. Seven of these clones were found to contain inserts with unique restriction enzyme maps representing overlapping genomic fragments spanning at least 30 kb. These inserts, LAMG-17, -19, -20, -28, -35, -37, and -47, were further digested and subcloned into plasmids. Detailed restriction maps of these subclones were made and compared to those of intact inserts to determine their correct locations (FIGS. 5A and 5B).

The correctness of the restriction map was verified with Southern blot analysis. DNA isolated from two B cell lines, BL and BJAB, and one T cell line, HSB-2, was digested to completion with Bam HI, Bal II, or Pvu II, size-fractionated, and transferred onto nitrocellulose. This filter was probed with the LAM-1 cDNA clone, pLAM-1. All genomic fragments derived from endonuclease digested DNA hybridized with cDNA probe to generate hybridizing bands of the appropriate size.

The pLAM-1 cDNA clone encodes an 85-bp 5' untranslated region. An oligonucleotide homologous with the 5' sequence of the pLAM-1 cDNA was used as a probe for primer extension analysis. This oligonucleotide was hybridized with poly (A$^+$) RNA isolated from the human B cell line RAJI, the LAM-1 negative human B cell line Namalwa, the mouse pre-B cell line A20, and yeast tRNA as a control. Complementary DNA was synthesized by extending the primer with reverse transcriptase. The major primer extension product obtained using the human LAM-1 positive B cell line RNA was extended 126 nucleotides beyond the translation initiation site. There was a single cluster of transcription initiation sites for the lyam-1 gene apparent in the reaction with RAJI RNA that was not found with the LAM-1 negative Namalwa RNA. Several primer extension products of size similar to those of the human B cell line RNA were obtained with mouse B cell RNA. Therefore, murine B cells may express an RNA species that cross-hybridizes with the oligonucleotide probe used. No primer extension products were obtained in the yeast tRNA control reactions.

The relationship of the primer extension results to the cloned LAM-1 cDNAs and the most 5' exon of lyam-1 isolated was used to determine the nucleotide sequence of the exon that encodes the translation initiation AUG codon. This exon ends immediately after the site that encodes the translation initiation codon (FIG. 6A) and overlaps precisely with the pLAM-1 cDNA sequence. The length of the cDNA clone obtained by Bowen et al., J. Cell Biol. 109:421–427 (1989) agrees precisely with the primer extension results except for two nucleotides. However, 15 nucleotides before the 5' end of the cDNA the sequence diverges from the genomic sequence at a site homologous with the 3' splice acceptor site consensus sequence. Therefore, it is most likely that this 15-bp region is derived from the exon upstream of this potential splice site. Thus, the primer extension results indicate that exon I would most likely be composed of 15 or fewer base pairs.

A 15-bp oligonucleotide homologous with the 5' nucleotides present in the cDNA clone of Bowen et al., supra but not encoded by exon II, was used to probe the 10 kb of cloned DNAs 5' of exon II; however, specific hybridization was not detected by Southern blot analysis. Under the conditions necessary for hybridization of this oligonucleotide, significant cross-hybridization occurred with λ-DNA, making it difficult to use this oligonucleotide to isolate the first exon from a λ-based genomic library.

These results suggest that the exon which encodes the translation initiation site is the second exon of the lyam-1 gene (FIG. 5C). Consistent with this, the 900 bp upstream of exon II did not contain any apparent "TATA" or "CCAAT" sequences frequently found in promoter regions of eukaryotic genes (FIG. 5). Therefore, it is likely that the transcription initiation region and exon I are further than 10 kb upstream from exon II of the lyam-1 gene. S1 nuclease protection analysis was carried out using the 5' region of exon II as a labeled probe for hybridization with poly (A$^+$) RNA from RAJI, Namalwa, and A20 cells. Two mRNA species were protected in the RAJI mRNA, while no S1 protection was provided by the other RNAs. The length of these fragments was consistent with differential splicing at the two potential CAG/N splice sites located within the potential splice acceptor site in exon II. It is therefore likely that the transcription initiation region has not been identified.

The majority of the exons were localized by comparison of the restriction enzyme maps of the genomic clones and the pLAM-1 cDNA. In cases where this method did not provide definitive results, subcloned DNA fragments were digested with selected restriction enzymes, electrophoresed through agarose gels, and transferred to nitrocellulose. Fragments containing exons were identified by Southern blot analysis using labeled cDNA or oligonucleotide probes. The exon that encodes the 3' untranslated region of the LAM-1 cDNA was not contained within the 30 kb of isolated DNA fragments. Therefore, a labeled 0.9-kb Dra I fragment containing most of the 3' untranslated region of the pLAM-1 cDNA was used as a probe to identify a homologous 3.2-kb fragment generated by complete Eco RI digestion of genomic DNA. Eco RI-digested genomic DNA fragments of this size were used to make a partial λ-gtII genomic library from which the 3.2-kb Eco RI fragment was cloned. This 3.2-kb fragment did not overlap with the previously isolated genomic DNAs.

The exact boundaries of the exons were determined by nucleotide sequence analysis. From this analysis, nine exons were identified which make up the entire pLAM-1 cDNA. Exon II encodes the translation initiation codon, and exon III encodes the leader domain of the LAM-1 protein (FIG. 6A). Each of the lectin-like, epidermal growth factor-like, transmembrane, and short consensus repeat domains was encoded by a separate exon. The smallest exon, IX, is 19 bp in length and may encode a carboxyl-terminal phosphorylation cassette. The last 5 amino acids of the LAM-1 protein and the 3' untranslated region which includes the poly(A) attachment site, AATAAA, are encoded by exon X as shown in FIG. 6C. The nine exons which encode pLAM-1 were split inside codons in all cases, except the junction between exons II and III. In each instance, the consensus sequences of 5' donor splice sites and 3' acceptor splice sites were adhered to. Nucleotide sequence polymorphisms within the coding region were observed between the genomic clones containing exon V that encoded SCR I and the pLAM-1 clone at cDNA nucleotide positions 741 and 747 (A to G), leading to a coding change from Asn to Ser in both cases, and at position 816 (A to G) changing the Glu to a Gly.

Experimental Procedures Construction of Chimeric Selectin cDNAs

Four new restriction endonuclease recognition sites were introduced separately into the pLAM-1 cDNA by polymerase chain reaction (PCR)-based site-directed mutagenesis as follows. Oligonucleotides surrounding and including each new restriction sequence were synthesized in both the sense and antisense directions. PCR was carried out using the new restriction site sense oligonucleotide and an antisense oligonucleotide anchor located in the plasmid near the 3' end of the cDNA. In a separate reaction, the new restriction site antisense oligonucleotide plus a sense oligonucleotide anchor from the plasmid 5' end were used to amplify the 5' end of the LAM-1 cDNA. The individual PCR products from these two reactions were gel purified, subcloned into the pSP65 vector (Promega Biotec, Madison, Wis.), digested with the appropriate restriction enzymes, and ligated together. The nucleotide changes were as follows: (a) $GA^{361}ATCC$ to GGATCC in the lectin domain, creating a BamHI site, corresponding to amino acid number 53 in the mature protein (FIG. 4A); (b) $A^{583}TGCAG$ to CTGCAG in the EGF domain, creating a PstI site, corresponding to amino acid number 127; (c) $GAGG^{881}C^{882}C$ to GAGCTC in the first SCR domain, creating a SacI site, corresponding to amino acid number 164; and (d) $GTCAAA^{1023}$ to GTCAAC in the second SCR domain, creating a HincII site, corresponding to amino acid number 279. The fidelity of the site-directed mutagenesis was confirmed by restriction mapping and sequence analysis of the cDNAs. Each of these sites is naturally present in the PADGEM cDNA (Larsen et al., Cell 59:305–312 (1984)).

Domain Mapping of Binding Sites

The chimeric selectin cDNAs were subcloned into the pMT-2 expression vector (Kaufman et al, J. Mol. Cell. Biol. 9:946–958 (1989)), and COS cells at ~50% confluency were transiently transfected with 3 µg of the indicated cDNA by the DEAE dextran method. One day after transfection, the COS cells were replated at ~50% confluency onto 35 mm Petri dishes (assay plates) (Bector-Dickinson, Lincoln Park, N.J.). The following day, HL-60 cells were washed twice in cold RPMI 1640 media (Gibco, Grand Island, N.Y.), resuspended in RPMI 1640 at a final concentration of $3.3 \times 10^6$ cells ml, and 0.6 ml ($2 \times 10^6$ cells) were added to assay plates which had been washed twice with cold RPMI 1640 media. The plates were gently rocked for 20 min at 4° C., washed five times, and the number of HL-60 cells bound to individual COS cells were counted on a minimum of 100 COS cells.

Assay for leukocyte attachment to HEV

The cDNAs encoding native L-selectin, L2P and L2P3L were subcloned into the Bam HI site of the pZIPneoSV(X) vector (Cepko et al, Cell 37:1053–1062 (1984)), and were used to transfect the mouse pre-B cell line 300.19. Stable transfectants were selected in medium containing 0.5–1.0 mg/ml G418 (geneticin; Sigma), and cells expressing the proteins were selected by panning with the LAM1–3 mAb (Spertini et al, J. Immunol. 147:942–949 (1991)). To generate P-selectin transfectants, the P-selectin cDNA in the pMT-2 vector was cotransfected with the pSV2neo vector containing the neomycin resistance marker. Rat lymph nodes were obtained from freshly euthanized Lewis rats, snap frozen in isopentane/liquid nitrogen, and stored at −70° C. in isopentane until use. For the HEV assay, $5 \times 10^6$ of each cell type were incubated on three 12 mm sections/slide at 64 rpm for 25 min at ~4° C., the excess cells were gently removed, and the slides were placed vertically in ice-cold fixative (PBS/2.4–6 glutaraldehyde) overnight. The slides were then counterstained with Gill's hematoxylin, overlaid with glycerol gelatin, and cover slips were applied. Each slide was scored for the number of lymphocytes bound/HEV. Between 100–200 HEV were counted for each experiment. Data are presented as mean±standard deviation of lymphocytes bound/HEV. ND, not determined.

Determination of neuraminidase sensitivity, protease sensitivity and $Ca^{2+}$ requirements for adhesion COS cells were transfected with the indicated cDNA and replated as described above. HL-60 cells were incubated in RPMI 1640 medium at 37° C. for two hours with either 0.25 U/ml *Clostridium perfringens* neuraminidase (Type VI, Sigma, St. Louis, Mo.), 50 mg/ml chymotrypsin or papain (Sigma), washed twice, and the assay was performed as described in the FIG. 2 legend. Neuraminidase treatment of the HL-60 cells was effective in eliminating all reactivity with the CSLEX1 anti-sLe$^x$ mAb (data not shown). In some groups, COS cells were preincubated with either 5 µg/ml GI mAb (a gift of Dr. R. P. McEver) (Geng et al, Nature 343:757–760 (1990)), or ascites fluid containing the LAM1–3 mAb (Spertini et al, J. Immunol. 147:942–949 (1991)) diluted 1:200. To determine the effect of EGTA, both the HL-60 cells and the COS cells were washed in RPMI 1640 containing 2.5 mM EGTA, and this medium was also used for the assay. No detachment of COS cells occurred under these conditions. These results are representative of at least four experiments.

Use

The adhesion of leukocytes to the endothelial wall of blood vessels and their infiltration into the surrounding tissues contributes to inflammation of tissue at the cellular level. Normally, the infiltrating leukocytes phagocytize invading organisms or dead or damaged cells. However, in pathologic inflammation, infiltrating leukocytes can cause serious and sometimes deadly damage. Leukocyte-mediated inflammation is involved in a number of human clinical manifestations, including the adult respiratory distress syndrome, multi-organ failure and reperfusion injury.

Local administration of therapeutic agents antagonistic to the function of the selectins can block competitively the adhesive interactions between leukocytes and the endothelium adjacent to an inflamed region. On a systemic level, treatment of a patient in shock (e.g., from a serious injury) with an antagonist to selectin function can result in the reduction of leukocyte migration and adhesion and the subsequent dramatic recovery of the patient.

Chimeric peptides or polypeptides combining ligand binding portions from within the lectin and EGF domains of two different selectins can be used for therapeutic treatment to interfere in the binding of leukocytes at the site of inflammation. Referring to FIG. 7, the close homology among the lectin and EGF domains of L-, P- and E-selectin can be seen, and the intron/exon organization of the respective genes encoding P- and E-selectin (Collins et al., J. Biol.Chem. 266:2466 (1991); Johnston et al., J. Biol. Chem.265:21381 (1990)) is the same as that of the lyam-1 gene encoding L-selectin, disclosed herein. These chimeric agents will offer more efficient targeting than using a single function antagonist. Therapeutic agents of the invention can also be used to block platelet or platelet and mononuclear cell aggregation, thus preventing throbus formation.

The therapeutic peptides or polypeptides can be composed solely of the indicated portions of lectin or EGF domains or they can include portions of any of the remaining domains (SCR, transmembrane or cytoplasmic), or the entire extracellular portion of a generic selectin molecule. The peptides or polypeptides also can be joined to a carrier protein (e.g., a soluble portion of an immunoglobulin molecule) to increase the serum half-life of the therapeutic agent. Immunoglobulin chimera are easily purified through standard immunochemistry procedures, including IgG-binding protein A-Sepharose chromatography. The chimera have the ability to form an immunoglobulin-like dimer with the concomitant higher avidity and serum half-life.

cDNA sequences encoding the chimeric polypeptides can be incorporated into replicable expression vectors and the vectors transfected into an appropriate host to express the encoded polypeptide. Stop codons can be incorporated into the DNA sequences or any other chain termination method can be used to prepare a soluble polypeptide. The expressed polypeptide can be purified by ordinary techniques well known to those of skill in the art, e.g., by affinity chromatographic methods.

Other agents can also be joined to the therapeutic polypeptides to form a useful product. For example, the ligand binding portions of the lectin and EGF domains of two different selectins can be combined with the toxic portion of a cytotoxin to produce a fusion protein. In addition, the selectin chimeric polypeptides may be coupled to a chemotherapeutic drug or drugs which could simultaneously bind to cells expressing their respective ligands, to administer the drug to a site of tissue damage or inflammation to treat, e.g., acute inflammation or vasculitis. Such drugs may include, anti-inflammatory agents or agents that provide regional relief from inflammatory distress. Syndromes, diseases, and conditions that could be treated by these agents would include, but not be limited to, treating inflammation, microbial/parasitic infections, post-reperfusion injury, leukemia, lymphoma, vasculitis, inhibition of the metastatic spread of tumor cells, organ transplantation, or graft rejection. As is well known to those of skill in the art, the fusion proteins can be transcribed from a hybrid cDNA molecule, or the agent may be covalently bonded to the chimeric polypeptide by routine procedures.

One method of imaging the sites of inflammation in a patient involves detecting the expression of the L-selectin ligand on the inflamed endothelium. The method includes administering to a patient a pharmaceutical composition consisting of a detectable amount of a labeled ligand binding fragment of L-selectin, alone or joined to a carrier protein, including a ligand binding portion of a different selectin receptor, in a pharmaceutically acceptable carrier. Sufficient time is allowed for the labeled polypeptide to localize at the site of L-selectin ligand expression, unbound polypeptide is permitted to clear from healthy tissue in the patient, and signal generated by the label is detected and converted into an image of the site of inflammation. The amount of labeled ligand binding fragment of L-selectin preferably would be from 1 pg/kg to 10 µg/kg although higher or lower doses are possible depending on the imaging agent label used and the sensitivity of the detection method.

Some of the labels which can be detected externally from within the body of a human patient include radionuclides, radiopaque labels, and paramagnetic isotopes. A radionuclide for in vivo diagnosis should have a half-life long enough that it is still detectable at the time of maximum uptake, but short enough that after diagnosis unwanted radiation does not remain in the patient. Coupling of radionuclides to antibodies or proteins is well known in the art (see, e.g., Daddona et al., U.S. Pat. No. 5,026,537, the teachings of which are incorporated by reference herein) and is often accomplished either directly or indirectly using an intermediary linking group. Examples of radioisotopes that could be used for in vivo diagnosis are $^{99}$Tc, $^{123}$I, $^{131}$I, $^{111}$In, $^{97}$Ru, $^{97}$Cu, $^{67}$Ga, $^{68}$Ga, $^{72}$As, $^{89}$Zr, and $^{201}$Ti. Paramagnetic isotopes for purposes of in vivo diagnosis can also be used according to the methods of this invention. Examples of elements that are particularly useful for use in magnetic resonance energy techniques include $^{157}$Gd, $^{55}$Mn, $^{162}$Dy, $^{52}$Cr, and $^{56}$Fe. For radiopaque imaging, the LAM-1 protein or ligand binding fragment is coupled to an agent that produces an opaque field at the site of inflammation upon X-ray imaging.

A ligand binding portion of the lectin or EGF-like domains of various selectins can be experimentally determined using this invention. In a typical procedure, fragments of the selectin cDNA can be fused with cDNA encoding a carrier protein, such as immunoglobulin heavy chain or another non-ligand binding portion of a different selectin. These chimeric proteins can be expressed on the cell surface, or as soluble molecules, and their ability to bind ligand assessed. Further segregated fragments of the lectin or EGF-like domain under study can be examined for their ability to bind ligands, as well as their ability to inhibit the binding of the parent selectin molecule to ligand.

Any of the peptides or polypeptides of the invention comprising lectin and EGF ligand binding portions from two different selectin molecules (including portions of any of the remaining domains (SCR, transmembrane or cytoplasic) of a generic selectin molecule or including a carrier protein) can be used to screen for antagonists of lectin or EGF function individually or for agents that can simultaneously antagonize the functions of the lectin and EGF domain of different selectins. This invention will allow the development of pharmacologic reagents composed of peptides, carbohydrate moieties, RNAs or other small molecules which may mimic the ligand of the lectin or EGF domains of the selectins or may mimic the ligand-binding epitopes of the respective selectin domains and thus be useful therapeutic agents.

In another therapeutic method, chimeric selectin polypeptides can be used in combination therapy with any other selectin or any other cell surface molecule, or soluble fragments thereof, involved in adhesion of leukocytes to endothelial surfaces. In addition, antagonists to any of the above receptors or receptor portions (or mAb reactive to the receptors or receptor portions) can be used in the above combinations or as independent antagonist combinations for treatment of a patient. Examples include ICAM-1, VCAM-1, VLA-4, CD18, CD11a, CD11b and CD31, and the mAb reactive with them.

The therapeutic agents may be administered orally, topically, or parenterally, (e.g., intranasally, subcutaneously, intramuscularly, intravenously, or intra-arterially) by routine methods in pharmaceutically acceptable inert carrier substances. Optimal dosage and modes of administration can readily be determined by conventional protocols.

The lyam-1 gene itself or portions thereof can be used to construct chimeric selectins. The gene can also be used in genetic therapy. Individuals having a genetic defect in the lyam-1 gene would be unable to produce a fully active L-selectin leukocyte "homing" receptor and thus would be unable to mobilize sufficient leukocytes to a site of inflammation. Individuals suspected of having a congenital defect in the lyam-1 gene could be screened for this genetic disorder using the sequence and structural information described. Treatment of affected individuals would then be possible using the lyam-1 gene or fragments thereof.

The normal regulation of the lyam-1 gene, as evidenced by the appearance and disappearance of L-selectin on the surface of a specific leukocyte sub-population can be monitored to test the effects of drugs or specific therapies that would alter gene expression.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

---

What is claimed is:

1. A method for inhibiting selectin mediated adhesion, migration and infiltration into tissues of cells expressing a selectin, comprising the step of administering a polypeptide selected from the group consisting of:
   (a) a polypeptide comprising the lectin domain of L-selectin and the EGF domain of P-selectin, or ligand-binding fragments thereof;
   (b) a polypeptide comprising the lectin domain of L-selectin and the EGF domain of E-selectin, or ligand-binding fragments thereof;
   (c) a polypeptide comprising the lectin domain of E-selectin and the EGF domain of P-selectin, or ligand-binding fragments thereof; and
   (d) a polypeptide comprising the lectin domain of P-selectin and the EGF domain of E-selectin, or ligand-binding fragments thereof;
in a pharmaceutically acceptable carrier substance.

2. The method according to claim 1, wherein the EGF domain of said polypeptide is followed by a selectin short consensus repeat (SCR) domain or a selectin SCR domain and a selectin transmembrane domain.

3. The method according to claim 2, wherein said selectin SCR domain and said selectin transmembrane domain are from the same selectin as the lectin domain.

4. The method according to any one of claims 1–3, wherein said polypeptide is joined to a therapeutic agent.

5. The method according to claim 4, wherein said therapeutic agent comprises either a chemotherapeutic drug or an anti-inflammatory agent.

6. The method according to any one of claims 1–3, wherein said polypeptide is joined to a carrier protein.

7. The method according to claim 6, wherein the polypeptide is joined to the N-terminus of an immunoglobulin heavy chain constant region.

8. The method according to claim 6, wherein said carrier protein comprises a non-ligand binding fragment of a selectin molecule.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
         ( A ) LENGTH: 2330 base pairs
         ( B ) TYPE: nucleic acid
         ( C ) STRANDEDNESS: single
         ( D ) TOPOLOGY: linear ( i i ) MOLECULE TYPE: cDNA ( i i i ) HYPOTHETICAL: NO ( i v ) ANTI-SENSE: NO ( i x ) FEATURE:
         ( A ) NAME/KEY: CDS
         ( B ) LOCATION: 53..1210

( x i ) SEQUENCE DESCRIPTION: SEQ ID NO:1:

```
GAATTCCCTT  TGGGCAAGGA  CCTGAGACCC  TTGTGCTAAG  TCAAGAGGCT  CA ATG                     55
                                                              Met
                                                               1

GGC  TGC  AGA  AGA  ACT  AGA  GAA  GGA  CCA  AGC  AAA  GCC  ATG  ATA  TTT  CCA        103
Gly  Cys  Arg  Arg  Thr  Arg  Glu  Gly  Pro  Ser  Lys  Ala  Met  Ile  Phe  Pro
               5                        10                       15

TGG  AAA  TGT  CAG  AGC  ACC  CAG  AGG  GAC  TTA  TGG  AAC  ATC  TTC  AAG  TTG        151
Trp  Lys  Cys  Gln  Ser  Thr  Gln  Arg  Asp  Leu  Trp  Asn  Ile  Phe  Lys  Leu
              20                        25                       30

TGG  GGG  TGG  ACA  ATG  CTC  TGT  TGT  GAT  TTC  CTG  GCA  CAT  CAT  GGA  ACC        199
Trp  Gly  Trp  Thr  Met  Leu  Cys  Cys  Asp  Phe  Leu  Ala  His  His  Gly  Thr
         35                        40                       45

GAC  TGC  TGG  ACT  TAC  CAT  TAT  TCT  GAA  AAA  CCC  ATG  AAC  TGG  CAA  AGG        247
Asp  Cys  Trp  Thr  Tyr  His  Tyr  Ser  Glu  Lys  Pro  Met  Asn  Trp  Gln  Arg
 50                        55                       60                        65

GCT  AGA  AGA  TTC  TGC  CGA  GAC  AAT  TAC  ACA  GAT  TTA  GTT  GCC  ATA  CAA        295
```

| | | | | | | | | | | | | | | |
|---|---|---|---|---|---|---|---|---|---|---|---|---|---|---|
| Ala | Arg | Arg | Phe | Cys | Arg | Asp | Asn | Tyr | Thr | Asp | Leu | Val | Ala | Ile | Gln |
| | | | | 70 | | | | 75 | | | | | 80 | | |

| | | | | | | | | | | | | | | | |
|---|---|---|---|---|---|---|---|---|---|---|---|---|---|---|---|
| AAC | AAG | GCG | GAA | ATT | GAG | TAT | CTG | GAG | AAG | ACT | CTG | CCT | TTC | AGT | CGT | 343 |
| Asn | Lys | Ala | Glu | Ile | Glu | Tyr | Leu | Glu | Lys | Thr | Leu | Pro | Phe | Ser | Arg |
| | | | 85 | | | | | 90 | | | | | 95 | | |

| TCT | TAC | TAC | TGG | ATA | GGA | ATC | CGG | AAG | ATA | GGA | GGA | ATA | TGG | ACG | TGG | 391 |
|---|---|---|---|---|---|---|---|---|---|---|---|---|---|---|---|---|
| Ser | Tyr | Tyr | Trp | Ile | Gly | Ile | Arg | Lys | Ile | Gly | Gly | Ile | Trp | Thr | Trp |
| | | 100 | | | | | 105 | | | | | 110 | | | |

| GTG | GGA | ACC | AAC | AAA | TCT | CTC | ACT | GAA | GAA | GCA | GAG | AAC | TGG | GGA | GAT | 439 |
|---|---|---|---|---|---|---|---|---|---|---|---|---|---|---|---|---|
| Val | Gly | Thr | Asn | Lys | Ser | Leu | Thr | Glu | Glu | Ala | Glu | Asn | Trp | Gly | Asp |
| | 115 | | | | | 120 | | | | | 125 | | | | |

| GGT | GAG | CCC | AAC | AAC | AAG | AAG | AAC | AAG | GAG | GAC | TGC | GTG | GAG | ATC | TAT | 487 |
|---|---|---|---|---|---|---|---|---|---|---|---|---|---|---|---|---|
| Gly | Glu | Pro | Asn | Asn | Lys | Lys | Asn | Lys | Glu | Asp | Cys | Val | Glu | Ile | Tyr |
| 130 | | | | | 135 | | | | | 140 | | | | | 145 |

| ATC | AAG | AGA | AAC | AAA | GAT | GCA | GGC | AAA | TGG | AAC | GAT | GAC | GCC | TGC | CAC | 535 |
|---|---|---|---|---|---|---|---|---|---|---|---|---|---|---|---|---|
| Ile | Lys | Arg | Asn | Lys | Asp | Ala | Gly | Lys | Trp | Asn | Asp | Asp | Ala | Cys | His |
| | | | | 150 | | | | | 155 | | | | | 160 | |

| AAA | CTA | AAG | GCA | GCC | CTC | TGT | TAC | ACA | GCT | TCT | TGC | CAG | CCC | TGG | TCA | 583 |
|---|---|---|---|---|---|---|---|---|---|---|---|---|---|---|---|---|
| Lys | Leu | Lys | Ala | Ala | Leu | Cys | Tyr | Thr | Ala | Ser | Cys | Gln | Pro | Trp | Ser |
| | | | 165 | | | | | 170 | | | | | 175 | | |

| TGC | AGT | GGC | CAT | GGA | GAA | TGT | GTA | GAA | ATC | ATC | AAT | AAT | TAC | ACC | TGC | 631 |
|---|---|---|---|---|---|---|---|---|---|---|---|---|---|---|---|---|
| Cys | Ser | Gly | His | Gly | Glu | Cys | Val | Glu | Ile | Ile | Asn | Asn | Tyr | Thr | Cys |
| | | 180 | | | | | 185 | | | | | 190 | | | |

| AAC | TGT | GAT | GTG | GGG | TAC | TAT | GGG | CCC | CAG | TGT | CAG | TTT | GTG | ATT | CAG | 679 |
|---|---|---|---|---|---|---|---|---|---|---|---|---|---|---|---|---|
| Asn | Cys | Asp | Val | Gly | Tyr | Tyr | Gly | Pro | Gln | Cys | Gln | Phe | Val | Ile | Gln |
| | 195 | | | | | 200 | | | | | 205 | | | | |

| TGT | GAG | CCT | TTG | GAG | GCC | CCA | GAG | CTG | GGT | ACC | ATG | GAC | TGT | ACT | CAC | 727 |
|---|---|---|---|---|---|---|---|---|---|---|---|---|---|---|---|---|
| Cys | Glu | Pro | Leu | Glu | Ala | Pro | Glu | Leu | Gly | Thr | Met | Asp | Cys | Thr | His |
| 210 | | | | | 215 | | | | | 220 | | | | | 225 |

| CCT | TTG | GGA | AAC | TTC | AAC | TTC | AAC | TCA | CAG | TGT | GCC | TTC | AGC | TGC | TCT | 775 |
|---|---|---|---|---|---|---|---|---|---|---|---|---|---|---|---|---|
| Pro | Leu | Gly | Asn | Phe | Asn | Phe | Asn | Ser | Gln | Cys | Ala | Phe | Ser | Cys | Ser |
| | | | | 230 | | | | | 235 | | | | | 240 | |

| GAA | GGA | ACA | AAC | TTA | ACT | GGG | ATT | GAA | GAA | ACC | ACC | TGT | GAA | CCA | TTT | 823 |
|---|---|---|---|---|---|---|---|---|---|---|---|---|---|---|---|---|
| Glu | Gly | Thr | Asn | Leu | Thr | Gly | Ile | Glu | Glu | Thr | Thr | Cys | Glu | Pro | Phe |
| | | | 245 | | | | | 250 | | | | | 255 | | |

| GGA | AAC | TGG | TCA | TCT | CCA | GAA | CCA | ACC | TGT | CAA | GTG | ATT | CAG | TGT | GAG | 871 |
|---|---|---|---|---|---|---|---|---|---|---|---|---|---|---|---|---|
| Gly | Asn | Trp | Ser | Ser | Pro | Glu | Pro | Thr | Cys | Gln | Val | Ile | Gln | Cys | Glu |
| | | 260 | | | | | 265 | | | | | 270 | | | |

| CCT | CTA | TCA | GCA | CCA | GAT | TTG | GGG | ATC | ATG | AAC | TGT | AGC | CAT | CCC | CTG | 919 |
|---|---|---|---|---|---|---|---|---|---|---|---|---|---|---|---|---|
| Pro | Leu | Ser | Ala | Pro | Asp | Leu | Gly | Ile | Met | Asn | Cys | Ser | His | Pro | Leu |
| | 275 | | | | | 280 | | | | | 285 | | | | |

| GCC | AGC | TTC | AGC | TTT | ACC | TCT | GCA | TGT | ACC | TTC | ATC | TGC | TCA | GAA | GGA | 967 |
|---|---|---|---|---|---|---|---|---|---|---|---|---|---|---|---|---|
| Ala | Ser | Phe | Ser | Phe | Thr | Ser | Ala | Cys | Thr | Phe | Ile | Cys | Ser | Glu | Gly |
| 290 | | | | | 295 | | | | | 300 | | | | | 305 |

| ACT | GAG | TTA | ATT | GGG | AAG | AAG | AAA | ACC | ATT | TGT | GAA | TCA | TCT | GGA | ATC | 1015 |
|---|---|---|---|---|---|---|---|---|---|---|---|---|---|---|---|---|
| Thr | Glu | Leu | Ile | Gly | Lys | Lys | Lys | Thr | Ile | Cys | Glu | Ser | Ser | Gly | Ile |
| | | | | 310 | | | | | 315 | | | | | 320 | |

| TGG | TCA | AAT | CCT | AGT | CCA | ATA | TGT | CAA | AAA | TTG | GAC | AAA | AGT | TTC | TCA | 1063 |
|---|---|---|---|---|---|---|---|---|---|---|---|---|---|---|---|---|
| Trp | Ser | Asn | Pro | Ser | Pro | Ile | Cys | Gln | Lys | Leu | Asp | Lys | Ser | Phe | Ser |
| | | | 325 | | | | | 330 | | | | | 335 | | |

| ATG | ATT | AAG | GAG | GGT | GAT | TAT | AAC | CCC | CTC | TTC | ATT | CCA | GTG | GCA | GTC | 1111 |
|---|---|---|---|---|---|---|---|---|---|---|---|---|---|---|---|---|
| Met | Ile | Lys | Glu | Gly | Asp | Tyr | Asn | Pro | Leu | Phe | Ile | Pro | Val | Ala | Val |
| | | 340 | | | | | 345 | | | | | 350 | | | |

| ATG | GTT | ACT | GCA | TTC | TCT | GGG | TTG | GCA | TTT | ATC | ATT | TGG | CTG | GCA | AGG | 1159 |
|---|---|---|---|---|---|---|---|---|---|---|---|---|---|---|---|---|
| Met | Val | Thr | Ala | Phe | Ser | Gly | Leu | Ala | Phe | Ile | Ile | Trp | Leu | Ala | Arg |
| | 355 | | | | | 360 | | | | | 365 | | | | |

| AGA | TTA | AAA | AAA | GGC | AAG | AAA | TCC | AAG | AGA | AGT | ATG | AAT | GAC | CCA | TAT | 1207 |
|---|---|---|---|---|---|---|---|---|---|---|---|---|---|---|---|---|
| Arg | Leu | Lys | Lys | Gly | Lys | Lys | Ser | Lys | Arg | Ser | Met | Asn | Asp | Pro | Tyr |
| 370 | | | | | 375 | | | | | 380 | | | | | 385 |

| | | | | | |
|---|---|---|---|---|---|
| TAAATCGCCC | TTGGTGAAAG | AAAATTCTTG | GAATACTAAA | AATCATGAGA | TCCTTTAAAT | 1267 |

| | | | | |
|---|---|---|---|---|
| CCTTCCATGA | AACGTTTTGT | GTGGTGGCAC | CTCCTACGTC | AAACATGAAG TGTGTTTCCT | 1327
| TCAGTGCATC | TGGGAAGATT | TCTACCTGAC | CAACAGTTCC | TTCAGCTTCC ATTTCACCCC | 1387
| TCATTTATCC | CTCAACCCCC | AGCCCACAGG | TGTTTATACA | GCTCAGCTTT TTGTCTTTTC | 1447
| TGAGGAGAAA | CAAATAAGAC | CATAAAGGGA | AAGGATTCAT | GTGGAATATA AAGATGGCTG | 1507
| ACTTTGCTCT | TTCTTGACTC | TTGTTTTCAG | TTTCAATTCA | GTGCTGTACT TGATGACAGA | 1567
| CACTTCTAAA | TGAAGTGCAA | ATTTGATACA | TATGTGAATA | TGGACTCAGT TTTCTTGCAG | 1627
| ATCAAATTTC | GCGTCGTCTT | CTGTATACGT | GGAGGTACAC | TCTATGAAGT CAAAAGTCTA | 1687
| CGCTCTCCTT | TCTTTCTAAC | TCCAGTGAAG | TAATGGGGTC | CTGCTCAAGT TGAAAGAGTC | 1747
| CTATTTGCAC | TGTAGCCTCG | CCGTCTGTGA | ATTGGACCAT | CCTATTTAAC TGGCTTCAGC | 1807
| CTCCCCACCT | TCTTCAGCCA | CCTCTCTTTT | TCAGTTGGCT | GACTTCCACA CCTAGCATCT | 1867
| CATGAGTGCC | AAGCAAAAGG | AGAGAAGAGA | GAAATAGCCT | GCGCTGTTTT TTAGTTTGGG | 1927
| GGTTTTGCTG | TTTCCTTTTA | TGAGACCCAT | TCCTATTTCT | TATAGTCAAT GTTTCTTTTA | 1987
| TCACGATATT | ATTAGTAAGA | AAACATCACT | GAAATGCTAG | CTGCAACTGA CATCTCTTTG | 2047
| ATGTCATATG | GAAGAGTTAA | AACAGGTGGA | GAAATTCCTT | GATTCACAAT GAAATGCTCT | 2107
| CCTTTCCCCT | GCCCCAGAC | CTTTTATCCA | CTTACCTAGA | TTCTACATAT TCTTTAAATT | 2167
| TCATCTCAGG | CCTCCCTCAA | CCCCACCACT | TCTTTTATAA | CTAGTCCTTT ACTAATCCAA | 2227
| CCCATGATGA | GCTCCTCTTC | CTGGCTTCTT | ACTGAAAGGT | TACCCTGTAA CATGCAATTT | 2287
| TGCATTTGAA | TAAAGCCTGC | TTTTTAAGTG | TTAAAAAGAA | TTC | 2330

( 2 ) INFORMATION FOR SEQ ID NO:2:

( i ) SEQUENCE CHARACTERISTICS:
        ( A ) LENGTH: 385 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Gly | Cys | Arg | Arg | Thr | Arg | Glu | Gly | Pro | Ser | Lys | Ala | Met | Ile | Phe |
|---|---|---|---|---|---|---|---|---|---|---|---|---|---|---|---|
| 1 | | | | 5 | | | | | 10 | | | | | 15 | |

| Pro | Trp | Lys | Cys | Gln | Ser | Thr | Gln | Arg | Asp | Leu | Trp | Asn | Ile | Phe | Lys |
|---|---|---|---|---|---|---|---|---|---|---|---|---|---|---|---|
| | | | 20 | | | | | 25 | | | | | 30 | | |

| Leu | Trp | Gly | Trp | Thr | Met | Leu | Cys | Cys | Asp | Phe | Leu | Ala | His | His | Gly |
|---|---|---|---|---|---|---|---|---|---|---|---|---|---|---|---|
| | | 35 | | | | | 40 | | | | | 45 | | | |

| Thr | Asp | Cys | Trp | Thr | Tyr | His | Tyr | Ser | Glu | Lys | Pro | Met | Asn | Trp | Gln |
|---|---|---|---|---|---|---|---|---|---|---|---|---|---|---|---|
| | 50 | | | | | 55 | | | | | 60 | | | | |

| Arg | Ala | Arg | Arg | Phe | Cys | Arg | Asp | Asn | Tyr | Thr | Asp | Leu | Val | Ala | Ile |
|---|---|---|---|---|---|---|---|---|---|---|---|---|---|---|---|
| 65 | | | | | 70 | | | | | 75 | | | | | 80 |

| Gln | Asn | Lys | Ala | Glu | Ile | Glu | Tyr | Leu | Glu | Lys | Thr | Leu | Pro | Phe | Ser |
|---|---|---|---|---|---|---|---|---|---|---|---|---|---|---|---|
| | | | | 85 | | | | | 90 | | | | | 95 | |

| Arg | Ser | Tyr | Tyr | Trp | Ile | Gly | Ile | Arg | Lys | Ile | Gly | Gly | Ile | Trp | Thr |
|---|---|---|---|---|---|---|---|---|---|---|---|---|---|---|---|
| | | | | 100 | | | | | 105 | | | | | 110 | |

| Trp | Val | Gly | Thr | Asn | Lys | Ser | Leu | Thr | Glu | Glu | Ala | Glu | Asn | Trp | Gly |
|---|---|---|---|---|---|---|---|---|---|---|---|---|---|---|---|
| | | | 115 | | | | | 120 | | | | | 125 | | |

| Asp | Gly | Glu | Pro | Asn | Asn | Lys | Lys | Asn | Lys | Glu | Asp | Cys | Val | Glu | Ile |
|---|---|---|---|---|---|---|---|---|---|---|---|---|---|---|---|
| | 130 | | | | | 135 | | | | | 140 | | | | |

| Tyr | Ile | Lys | Arg | Asn | Lys | Asp | Ala | Gly | Lys | Trp | Asn | Asp | Asp | Ala | Cys |
|---|---|---|---|---|---|---|---|---|---|---|---|---|---|---|---|
| 145 | | | | | 150 | | | | | 155 | | | | | 160 |

| His | Lys | Leu | Lys | Ala | Ala | Leu | Cys | Tyr | Thr | Ala | Ser | Cys | Gln | Pro | Trp |
|---|---|---|---|---|---|---|---|---|---|---|---|---|---|---|---|

|     |     |     |            | 165 |     |     |            | 170 |     |     |            | 175 |     |     |
|-----|-----|-----|------------|-----|-----|-----|------------|-----|-----|-----|------------|-----|-----|-----|

Ser Cys Ser Gly His Gly Glu Cys Val Glu Ile Ile Asn Asn Tyr Thr
            180             185                 190

Cys Asn Cys Asp Val Gly Tyr Tyr Gly Pro Gln Cys Gln Phe Val Ile
        195             200             205

Gln Cys Glu Pro Leu Glu Ala Pro Glu Leu Gly Thr Met Asp Cys Thr
    210             215             220

His Pro Leu Gly Asn Phe Asn Phe Asn Ser Gln Cys Ala Phe Ser Cys
225                 230             235                     240

Ser Glu Gly Thr Asn Leu Thr Gly Ile Glu Glu Thr Thr Cys Glu Pro
            245             250             255

Phe Gly Asn Trp Ser Ser Pro Glu Pro Thr Cys Gln Val Ile Gln Cys
            260             265             270

Glu Pro Leu Ser Ala Pro Asp Leu Gly Ile Met Asn Cys Ser His Pro
        275             280             285

Leu Ala Ser Phe Ser Phe Thr Ser Ala Cys Thr Phe Ile Cys Ser Glu
    290             295             300

Gly Thr Glu Leu Ile Gly Lys Lys Thr Ile Cys Glu Ser Ser Gly
305             310             315                     320

Ile Trp Ser Asn Pro Ser Pro Ile Cys Gln Lys Leu Asp Lys Ser Phe
            325             330             335

Ser Met Ile Lys Glu Gly Asp Tyr Asn Pro Leu Phe Ile Pro Val Ala
            340             345             350

Val Met Val Thr Ala Phe Ser Gly Leu Ala Phe Ile Ile Trp Leu Ala
        355             360             365

Arg Arg Leu Lys Lys Gly Lys Lys Ser Lys Arg Ser Met Asn Asp Pro
        370             375             380

Tyr
385

( 2 ) INFORMATION FOR SEQ ID NO:3:

( i ) SEQUENCE CHARACTERISTICS:
        ( A ) LENGTH: 1192 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

```
AGAGAGCTGT  TATAAAGATT  AAACAATATA  ATAAATATGG  CGCGTGAGCT  TCAGAGTTTT        60
TGTTGTTGTT  ATTATTATTT  TCCTAAAAAT  GCAAATCTGA  TTTGCATTTG  ACTCATTGAC       120
TCACATCAGT  GGGTCTTCCT  TTTTATTGTC  CTTCATCATA  TGGGTCCTAA  TTTCACATGC       180
AGTCTTATAA  AACCATCTCA  TTTTATAGTC  CAAGAATATT  AAAGGTACTT  GTAGGCTCCC       240
AAACCTACAC  GGTGAAAAGC  TAGAGAGCAT  GGGCTCTCTT  CAGGGGTTAA  CTTCAGGAAG       300
TGCCACTAAC  AAGGACGTCC  ACTAGGTGGT  GAGCAAGGAA  AGACGGAGGT  GAAGGAACCG       360
AAACGAGTCA  AGTCCACTGC  TTAGCTCTAC  TGAAGTTTTG  CAAACATCAT  AAATATGTCT       420
GAAATGCAGT  TTTGATTTGT  AGTATTTGCA  ATTTCCAAGG  GCCATTTACC  ACAGGTAGCC       480
AAGAGTTAGT  TTAGCATTTA  TGAAAAAGAT  AGGGGAGGGT  GGTGGTTAAG  AAGGAGGTGG       540
AGGAGAGAGT  GAAGGAGGAA  GAGGAGAACA  AGAACCAAAC  AAAAACAAGA  ACAAGAACAA       600
```

| | | | | | | |
|---|---|---|---|---|---|---|
| GTAGAAGAAG | AGGAGCAGGG | AGGAAAAAGA | AGAGGAAGAA | GAACAGCAAC | AACAATGAGT | 660 |
| GAAGGAGGAG | GAGGGTAAGG | AAAGATGCAT | AGGAGAATGG | AAGGAAGGAT | AGAAAGGAGG | 720 |
| GAAGGAAGAG | AGAATCTAGT | CACATTACTT | TCTGATCAGC | AGTTCATTTT | TGTCTCAGTG | 780 |
| GGAGGCAATA | GAGGCCAGTC | TAGGAAAGGG | GTGGGGAAAG | AGGAAAGAGA | AGTGCAGGAG | 840 |
| GAAGGGGAGG | CCCAAGGGGA | GGAGGAGGAG | GATGTGAGAC | TGGGTTAGAG | AAATGAAAGA | 900 |
| AAGCAAGGCT | TTCTGTTGAC | ATTCAGTGCA | GTCTACCTGC | AGCACAGCAC | ACTCCCTTTG | 960 |
| GGCAAGGACC | TGAGACCCTT | GTGCTAAGTC | AAGAGGCTCA | ATGGGCTGCA | GAAGAACTAG | 1020 |
| AGAAGGACCA | AGCAAAGCCA | TGGTGAGCCT | TTCAGCCTAA | AAGACGTTTA | GATGCTCAGA | 1080 |
| TAGAAACTCT | TGGGGTTGTA | GAGGCAGGTG | GCAAGGATAG | GAATCACCCC | ATTTCAATTC | 1140 |
| TGGTTTTAAA | TAATATAGAA | ACTAAACATT | TTCTCAGACC | CTCAAAAAAA | GT | 1192 |

( 2 ) INFORMATION FOR SEQ ID NO:4:

( i ) SEQUENCE CHARACTERISTICS:
        ( A ) LENGTH: 363 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:4:

| | | | | | | |
|---|---|---|---|---|---|---|
| CACTGAGACT | AAGCGTAAAA | TAAATAGAAC | AAACAAACTG | TGCATCAGTT | CTGATGTAAA | 60 |
| TTTGAAGTAA | TTTTCATCTA | TGTCTGAGAA | ACCTGTTACC | TCAGACAGGG | TTAGTAGACA | 120 |
| TATGTGTTTT | ATTCTGATTA | TTAAGAAAGT | TGTAAGCACC | ACCTCAAAGG | CTATAAATGT | 180 |
| GTGGTTTAAG | GGTATACATC | TAAATATAAT | TTTGTATTTC | ATTTGCAGAT | ATTTCCATGG | 240 |
| AAATGTCAGA | GCACCCAGAG | GGACTTATGG | AACATCTTCA | AGTTGTGGGG | GTGGACAATG | 300 |
| CTCTGTTGTG | GTATGTTATG | ATATTTATAT | ATCACTAAGT | CTATTTACT | TATATTCATT | 360 |
| TTT | | | | | | 363 |

( 2 ) INFORMATION FOR SEQ ID NO:5:

( i ) SEQUENCE CHARACTERISTICS:
        ( A ) LENGTH: 531 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:5:

| | | | | | | |
|---|---|---|---|---|---|---|
| CTGGAGTAGT | GCTAGGTTCT | TTTTAGCTGT | AACATTATGT | AAGTCTGCAT | AGGTCACACT | 60 |
| GATGTCTTGC | AGATTTCCTG | GCACATCATG | GAACCGACTG | CTGGACTTAC | CATTATTCTG | 120 |
| AAAACCCAT | GAACTGGCAA | AGGGCTAGAA | GATTCTGCCG | AGACAATTAC | ACAGATTTAG | 180 |
| TTGCCATACA | AAACAAGGCG | GAAATTGAGT | ATCTGGAGAA | GACTCTGCCT | TTCAGTCGTT | 240 |
| CTTACTACTG | GATAGGAATC | CGGAAGATAG | GAGGAATATG | GACGTGGGTG | GGAACCAACA | 300 |
| AATCTCTCAC | TGAAGAAGCA | GAGAACTGGG | GAGATGGTGA | GCCCAACAAC | AAGAAGAACA | 360 |

| | | | | | |
|---|---|---|---|---|---|
| AGGAGGACTG | CGTGGAGATC | TATATCAAGA | GAAACAAAGA | TGCAGGCAAA | TGGAACGATG | 420
| ACGCCTGCCA | CAAACTAAAG | GCAGCCCTCT | GTTACACAGG | TAGGGAGTGA | CAAGACGGCT | 480
| ATGCTGCCTC | AGACTCAGGA | AGGGCCACGG | TTAAGAGAAT | ACTCAGATTT | A | 531

( 2 ) INFORMATION FOR SEQ ID NO:6:

( i ) SEQUENCE CHARACTERISTICS:
        ( A ) LENGTH: 832 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:6:

| | | | | | |
|---|---|---|---|---|---|
| AAAATTTTAG | CCATATGATT | TTTATGCTAT | GAATTTACCA | AATAAACCTT | TCCTGATTAT | 60
| TTAAATCATC | TCAGACAAAA | GGTTATCTAT | GTCTAAAGAA | ATGACTTTGA | GTACTAAAAT | 120
| GTAATCACAT | TAAAATATTT | TTTTTCTGAC | CTCCTTAAAG | CTTCTTGCCA | GCCCTGGTCA | 180
| TGCAGTGGCC | ATGGAGAATG | TGTAGAAATC | ATCAATAATT | ACACCTGCAA | CTGTGATGTG | 240
| GGGTACTATG | GGCCCCAGTG | TCAGTTTGGT | AAGTCTCTTT | CCTTTCTTTG | CTTCTTCTTA | 300
| GGTAAAGTCA | CAGGAATCAT | TATAGCTTAT | CATGAAGCTG | GTTGGAACAA | AATGATACTA | 360
| GCCACTCTGA | GAAATGGGAA | GTTTTGATCA | GAAAGCTCTG | CTTTCACAAT | ATTGTTACCT | 420
| TTCCGTAAAG | ATTTCATAAG | TCAGCATGAA | GTTTCGATTC | ACTTCTCAAC | AAGTCTTTTT | 480
| GAGTACCACA | AGAAGCACAG | TGTTGGGATA | AAGCTGTCAG | GGTTACAATA | AGGAATTAGC | 540
| ATGGTAGATT | CCCGCTCTCA | AGAAGCTCAC | GATCTAATGA | GCTTGTTAGA | TTAATTAGAA | 600
| CTCTAAGGTC | TGGAAGAAAC | TATGCCATTT | ATCATTAGGA | GGCTGAGTTA | CCCAGAAAGT | 660
| ATCTTGCTTT | TTCCTTCTAG | TAGTTCCTTT | CCTTCTTGCA | GTTCTCCACA | CTTAACACAT | 720
| GTGCTCTGTA | GCACACTGAC | TTTGCTGGTG | GCCTTCTCTC | TCATTTTGCA | CATGGCCAAA | 780
| AAACATGTCA | TCTTTAAGAC | ATTGTTCAAA | GACAGTTTCT | TCTAGGAAGC | TT | 832

( 2 ) INFORMATION FOR SEQ ID NO:7:

( i ) SEQUENCE CHARACTERISTICS:
        ( A ) LENGTH: 712 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:7:

| | | | | | |
|---|---|---|---|---|---|
| CTCTGATGTG | ATAGTTATTT | CCCGACTAAG | CTGGTCATTC | CCAGTTACAC | CTATTTGGCT | 60
| TTAAGGATTC | TCACTACAGA | TAATACTGAA | GATAATAATA | TGAAGACTAG | CTAATGTTTA | 120
| CTTAGAATTT | CTGATGAGTC | AGGCTTTGTT | CTAACGTCCT | TGACTTATGC | TAATTGAATT | 180
| ACATTTAGTT | TCCATATCAA | TTTGATAAAG | ATAACACAAT | TTCATTATTC | CTCTTATATA | 240
| GATGAAGAAA | CTGAAGTTGG | AGGGTTCAAG | TAACCTTGTT | TAAAGGCACA | TGGTTATCAA | 300
| GTGGCAGGGC | TAGGATTCAA | ATCCAGGCGT | CAGTTCCTCT | TAACTCTTCC | CCATACTGTT | 360

```
TCTTTCCCTA  TTGAAGTGAT  TCAGTGTGAG  CCTTTGGAGG  CCCCAGAGCT  GGGTACCATG    420

GACTGTACTC  ACCCTTTGGG  AAACTTCAGC  TTCAGCTCAC  AGTGTGCCTT  CAGCTGCTCT    480

GAAGGAACAA  ACTTAACTGG  GATTGAAGAA  ACCACCTGTG  GACCATTTGG  AAACTGGTCA    540

TCTCCAGAAC  CAACCTGTCA  AGGTGAGTAA  CTTCAGACTA  GAGGTTTTGT  CATGCAATCC    600

TGGGCTTACA  GTCAGAACAT  TCAGTAGAAG  TTTGCTGAGA  AGTCAAACTT  AGGATCCTAA    660

TTTAACCTAA  CTTTTGTTTA  ACCTACTGTG  ATGTTTCTCA  AAGGACTTAT  TC            712
```

( 2 ) INFORMATION FOR SEQ ID NO:8:

( i ) SEQUENCE CHARACTERISTICS:
          ( A ) LENGTH: 451 base pairs
          ( B ) TYPE: nucleic acid
          ( C ) STRANDEDNESS: single
          ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:8:

```
GAGGGTCACC  TTAGCTAGGG  CAGCAGCCTG  GAGTAGCTAC  TCCTCTCCCC  ACAGCTTTCA     60

ATGCTTCCTT  GCCTTCATCT  CTCATTCACC  ACCCACCATC  ATTCTCAAGA  AAATAAAGCC    120

TGGAAGCAAT  ATCACAAGTA  ATGTAGTCAG  GCAGCTTTGG  CTAAAAATCC  AAAGCTCAAG    180

GGAGGGTCTC  TACTCAGAAA  TACTGTTTTG  TCTTTTTTTT  TTTTCTTTT   TCATTGAAGT    240

GATTCAGTGT  GAGCCTCTAT  CAGCACCAGA  TTTGGGGATC  ATGAACTGTA  GCCATCCCCT    300

GGCCAGCTTC  AGCTTTACCT  CTGCATGTAC  CTTCATCTGC  TCAGAAGGAA  CTGAGTTAAT    360

TGGGAAGAAG  AAAACCATTT  GTGAATCATC  TGGAATCTGG  TCAAATCCTA  GTCCAATATG    420

TCAAAGTGAG  TAAGTTTGTC  CTGGAACTGA  A                                    451
```

( 2 ) INFORMATION FOR SEQ ID NO:9:

( i ) SEQUENCE CHARACTERISTICS:
          ( A ) LENGTH: 544 base pairs
          ( B ) TYPE: nucleic acid
          ( C ) STRANDEDNESS: single
          ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:9:

```
TATCAGAACT  AAGAAAGCTT  GGGCTGCAGG  TCGACTCTAG  GTGCATTTTC  AGGAACTCTA     60

TGAACCACAA  ATCTGGGCAT  TGAGATTCTG  TAGGCATTAG  ACTAGCAAGG  CTGGTCAGTC    120

TTTGCCTATG  CTGTAGACTC  ATCAGGGGCC  TTCCCATGCC  AGTTTCCTCA  TCTGTCAAAT    180

GGCATCATTT  GGGCTACTAC  TGGGAGATGT  AAGGAGGAAA  AAAGTCAAAT  ATCATGAGAT    240

AGACTAAGGA  AATAATGCTG  GTGGTCTCAT  GCTATGTGCC  TTACTGATTT  CTCTTTCAGA    300

ATTGGACAAA  AGTTTCTCAA  TGATTAAGGA  GGGTGATTAT  AACCCCTCT   TCATTCCAGT    360

GGCAGTCATG  GTTACTGCAT  TCTCTGGGTT  GGCATTTATC  ATTTGGCTGG  CAAGGAGATT    420

AAAAAAAGGT  ATGTGAGTTT  AACTTCACAT  GAAAAGAACA  CAACTTTAAA  GTGAAAAGA     480

AAAAAAAAAG  AAACCCACAG  GAAATTAAAT  GTGATAGATT  CAACACAAGC  AGGATGCCAA    540
```

GCTT 544

(2) INFORMATION FOR SEQ ID NO:10:

(i) SEQUENCE CHARACTERISTICS:
        (A) LENGTH: 524 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:10:

| | | | | | | |
|---|---|---|---|---|---|---|
| TAGTTTACAG | TATTAGCAGC | TGTCCCTCAA | GGAAGAATCT | GCAGGTAGAT | GAGATGCAGA | 60 |
| TTGGGTGGGA | TAAACACTTG | AATGACATAT | TGGGTCTTGC | CACCAGGCAA | TTTAGCAATT | 120 |
| CTGTCTTCTT | GAGTAGCACG | GAGATGGAAT | GGAACCTCAG | GAGGCATCTG | CATCAACATG | 180 |
| TCTGTTCTGT | ATTAGTGTCT | ACCACTGTTT | ATTAAGCCAG | TTCCTCAAAT | CTCCTTTGAC | 240 |
| ACAGATAGGG | TCCACCTAAC | AAATACCTAA | TATACTTCAA | AAGACAGTTT | TGAGAGTGGG | 300 |
| AGTCTTCCTT | CTCCCTTACT | TGAAAAACTT | TAAATTGTCT | AATTTTGCT | AATGCCTTTT | 360 |
| TCTCTATTTT | CTATTTCAGG | CAAGAAATCC | AAGAGAAGGT | AAGTTTATT | AGTGGCGAGG | 420 |
| AGTTTCCACA | TCTGCTGATT | CATTCTCTAC | TTCTTAAGTT | ACTTCTGCTC | TAGCTAGACA | 480 |
| CATACCCATA | GTAGTTATTA | CTGGGTCTAT | CAATGACAGA | TAGG | | 524 |

(2) INFORMATION FOR SEQ ID NO:11:

(i) SEQUENCE CHARACTERISTICS:
        (A) LENGTH: 1696 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:11:

| | | | | | | |
|---|---|---|---|---|---|---|
| ATAAGCATCA | CTAAAGAGCT | TGTTAGGGGT | GCAGAATCTC | AGGCTCCACT | CAGACCTACT | 60 |
| GAATCAGAGT | CTGCATTTTA | ACACCATCTC | TGAGTGGTAA | GGACATGAAA | ATCTGAGAAG | 120 |
| TGCTGCTACT | AGGGTTTGCT | TACATTTGTT | CATCTTCAGA | GGTTCCTAAA | GCCTGGCCTC | 180 |
| TTGTCTGAGA | TTTCCAGCTG | AAAGCATTTC | CTTGCTCCTC | TTCTCATCTC | TAATGAATAT | 240 |
| TTACCTTTAC | TACTAACACT | CCAAGTTTTG | CAATTTTTAA | ACTCTTATTA | TCTTTTGTTT | 300 |
| TTCTTTCAGT | ATGAATGACC | CATATTAAAT | CGCCCTTGGT | GAAAGAAAAT | TCTTGGAATA | 360 |
| CTAAAAATCA | TGAGATCCTT | TAAATCCTTC | CATGAAACGT | TTTGTGTGGT | GGCACCTCCT | 420 |
| ACGTCAAACA | TGAAGTGTGT | TTCCTTCAGT | GCATCTGGGA | AGATTTCTAC | CTGACCAACA | 480 |
| GTTCCTTCAG | CTTCCATTTC | ACCCCTCATT | TATCCCTCAA | CCCCCAGCCC | ACAGGTGTTT | 540 |
| ATACAGCTCA | GCTTTTTGTC | TTTTCTGAGG | AGAAACAAAT | AAGACCATAA | AGGGAAAGGA | 600 |
| TTCATGTGGA | ATATAAAGAT | GGCTGACTTT | GCTCTTTCTT | GACTCTTGTT | TTCAGTTTCA | 660 |
| ATTCAGTGCT | GTACTTGATG | ACAGACACTT | CTAAATGAAG | TGCAAATTTG | ATACATATGT | 720 |
| GAATATGGAC | TCAGTTTTCT | TGCAGATCAA | ATTTCGCGTC | GTCTTCTGTA | TACGTGGAGG | 780 |

| | | | | | | |
|---|---|---|---|---|---|---|
| TACACTCTAT | GAAGTCAAAA | GTCTACGCTC | TCCTTTCTTT | CTAACTCCAG | TGAAGTAATG | 840 |
| GGGTCCTGCT | CAAGTTGAAA | GAGTCCTATT | TGCACTGTAG | CCTCGCCGTC | TGTGAATTGG | 900 |
| ACCATCCTAT | TTAACTGGCT | TCAGCCTCCC | CACCTTCTTC | AGCCACCTCT | CTTTTTCAGT | 960 |
| TGGCTGACTT | CCACACCTAG | CATCTCATGA | GTGCCAAGCA | AAAGGAGAGA | AGAGAGAAAT | 1020 |
| AGCCTGCGCT | GTTTTTAGT | TTGGGGGTTT | TGCTGTTTCC | TTTTATGAGA | CCCATTCCTA | 1080 |
| TTTCTTATAG | TCAATGTTTC | TTTTATCACG | ATATTATTAG | TAAGAAAACA | TCACTGAAAT | 1140 |
| GCTAGCTGCA | ACTGACATCT | CTTTGATGTC | ATATGGAAGA | GTTAAAACAG | GTGGAGAAAT | 1200 |
| TCCTTGATTC | ACAATGAAAT | GCTCTCCTTT | CCCCTGCCCC | CAGACCTTTT | ATCCACTTAC | 1260 |
| CTAGATTCTA | CATATTCTTT | AAATTTCATC | TCAGGCCTCC | CTCAACCCCA | CCACTTCTTT | 1320 |
| TATAACTAGT | CCTTTACTAA | TCCAACCCAT | GATGAGCTCC | TCTTCCTGGC | TTCTTACTGA | 1380 |
| AAGGTTACCC | TGTAACATGC | AATTTTGCAT | TTGAATAAAG | CCTGCTTTTT | AAGTGTTAAC | 1440 |
| TAGTTTGCCT | AGTTTGTTAT | TTTGAAAATT | GATCATATGT | TTTGTTTCT | CCCCAGTGAG | 1500 |
| TTACATGCTC | CTTCAGGGCA | GAGTTTGTGT | CAGATCCCTG | GAGTATCTAG | TGCATTACTT | 1560 |
| GACACTCAAT | AAATGAATGT | TCAAATAAAT | CAGAAAGAGC | ATACAGTGCA | CTGCTGATAT | 1620 |
| AAGTTTCAGC | ATCCCTCTTT | CTCTATGGCA | TCTGATGACC | TGGGTCAGAT | ATCACCTAAT | 1680 |
| GTCAACAGCT | GAATTC | | | | | 1696 |